(12) United States Patent
Blankenship et al.

(10) Patent No.: US 10,792,201 B2
(45) Date of Patent: Oct. 6, 2020

(54) DOCKING SYSTEMS FOR MEDICAL DEVICES AND RELATED DEVICES

(71) Applicant: Skytron, LLC, Grand Rapids, MI (US)

(72) Inventors: Samuel A. Blankenship, Anoka, MN (US); Peter B. Blankenship, Anoka, MN (US); Richard Baumhardt, Breckenridge, MN (US)

(73) Assignee: Skytron, LLC, Grand Rapids, MI (US)

( * ) Notice: Subject to any disclaimer, the term of this patent is extended or adjusted under 35 U.S.C. 154(b) by 203 days.

(21) Appl. No.: 15/888,788

(22) Filed: Feb. 5, 2018

(65) Prior Publication Data

US 2018/0153749 A1 Jun. 7, 2018

Related U.S. Application Data

(63) Continuation of application No. 15/130,005, filed on Apr. 15, 2016, now Pat. No. 9,883,978.

(60) Provisional application No. 62/210,724, filed on Aug. 27, 2015, provisional application No. 62/207,106, filed on Aug. 19, 2015, provisional application No. 62/148,398, filed on Apr. 16, 2015.

(51) Int. Cl.
| | |
|---|---|
| *A61G 5/10* | (2006.01) |
| *A61G 7/05* | (2006.01) |
| *A61M 5/14* | (2006.01) |
| *A61G 12/00* | (2006.01) |

(52) U.S. Cl.
CPC ............. *A61G 5/10* (2013.01); *A61G 5/1094* (2016.11); *A61G 7/0503* (2013.01); *A61M 5/1413* (2013.01); *A61M 5/1414* (2013.01); *A61M 5/1415* (2013.01); *A61G 12/008* (2013.01); *A61G 2203/80* (2013.01)

(58) Field of Classification Search
CPC ... A61G 7/0503; A61G 7/1044; A61G 7/1415
See application file for complete search history.

(56) References Cited

U.S. PATENT DOCUMENTS

| | | | | |
|---|---|---|---|---|
| 4,945,592 A * | 8/1990 | Sims | .................... | A61G 7/05 248/129 |
| 5,898,961 A * | 5/1999 | Ambach | .................. | A61G 7/05 292/108 |
| 6,585,206 B2 * | 7/2003 | Metz | .................... | A61G 7/0503 248/121 |
| 7,065,811 B2 * | 6/2006 | Newkirk | ............. | A61M 5/1415 5/600 |
| 7,065,812 B2 * | 6/2006 | Newkirk | ............. | A61G 7/0503 248/125.8 |
| 7,865,983 B2 * | 1/2011 | Newkirk | .................. | A61G 7/05 5/503.1 |
| 9,528,536 B2 * | 12/2016 | Bally | .................... | F16M 13/022 |
| 2009/0142172 A1 * | 6/2009 | Blankenship | ....... | A61M 5/1415 414/495 |
| 2013/0181100 A1 * | 7/2013 | Blankenship | ....... | A61M 5/1415 248/129 |

(Continued)

*Primary Examiner* — Kevin Hurley
(74) *Attorney, Agent, or Firm* — Warner Norcross + Judd LLP

(57) ABSTRACT

Embodiments of the invention relate to docking systems for poles or other devices that can hold medical and/or accessory equipment, typically in a clinical or hospital environment, and can include associated docking systems for various devices such as beds, wheelchairs, walkers, wagons, and the like.

20 Claims, 38 Drawing Sheets

(56) References Cited

U.S. PATENT DOCUMENTS

2015/0157522 A1\* 6/2015 Blankenship ........ A61G 12/008
 224/547
2016/0000995 A1 1/2016 Blankenship et al.

\* cited by examiner

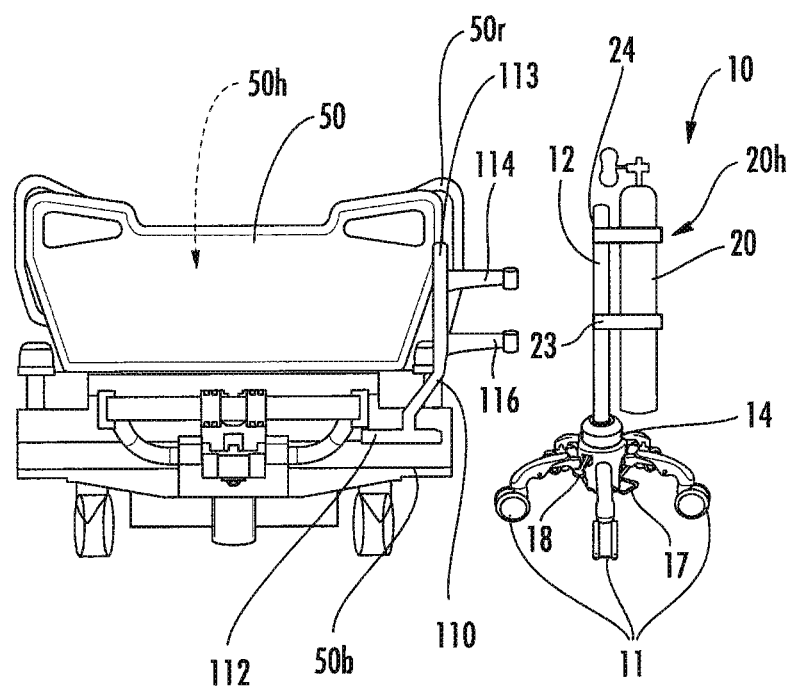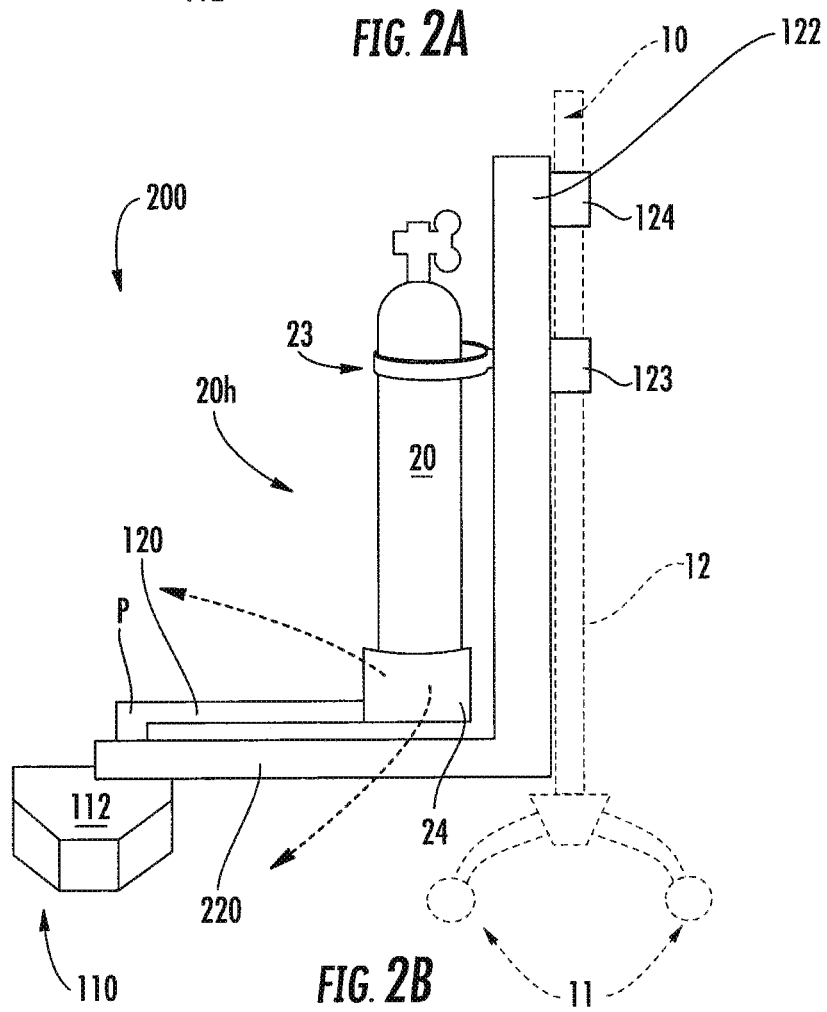

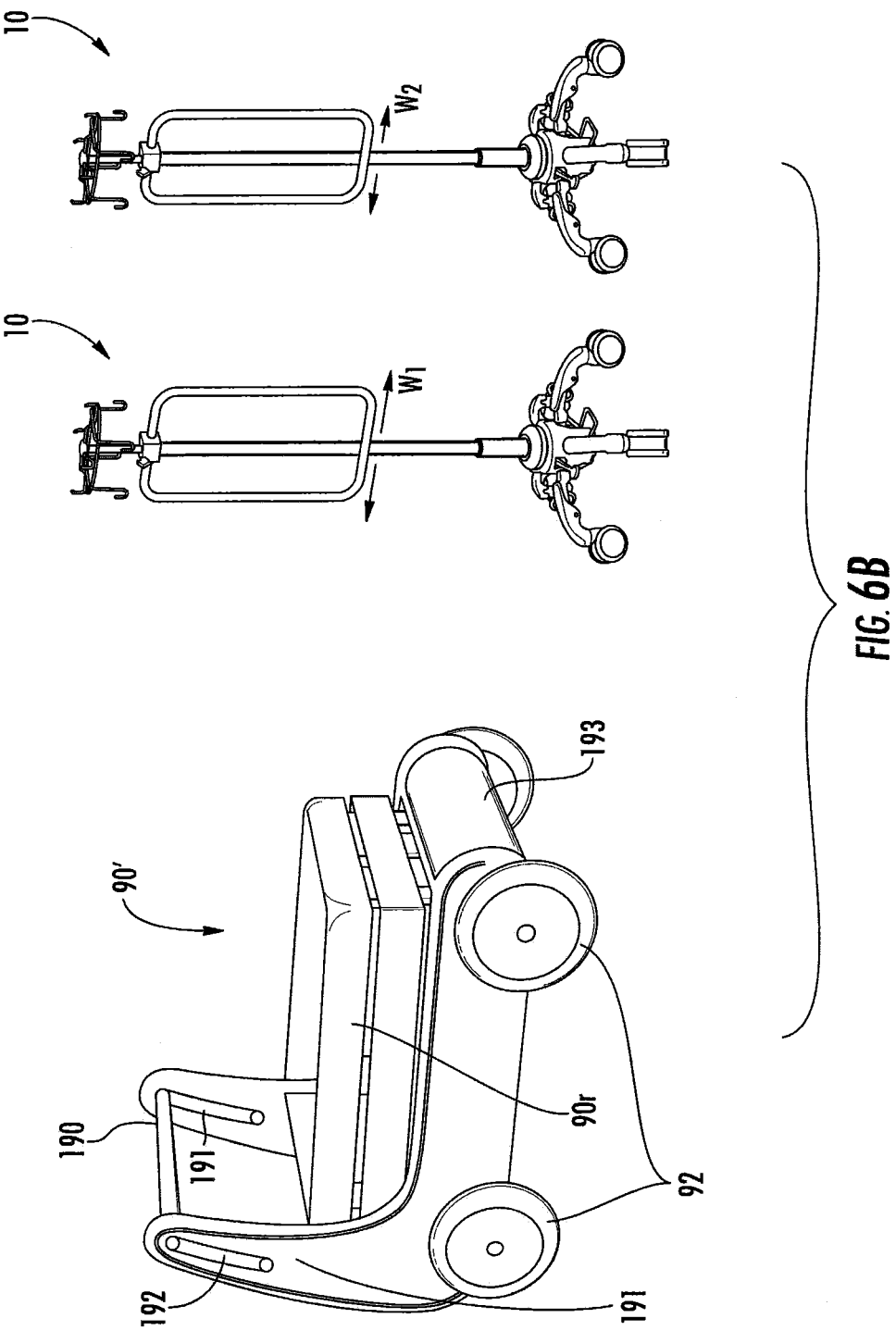

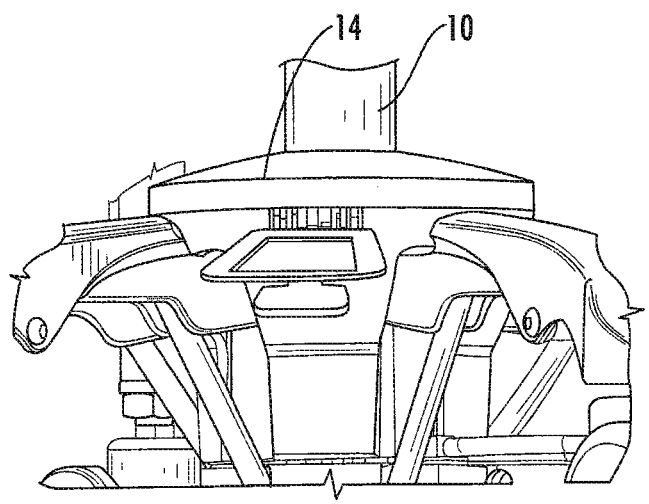
FIG. 9E
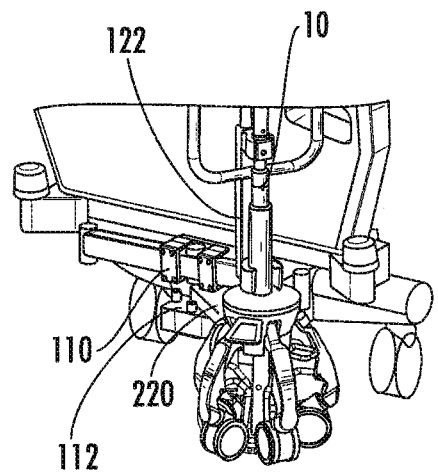
FIG. 9F
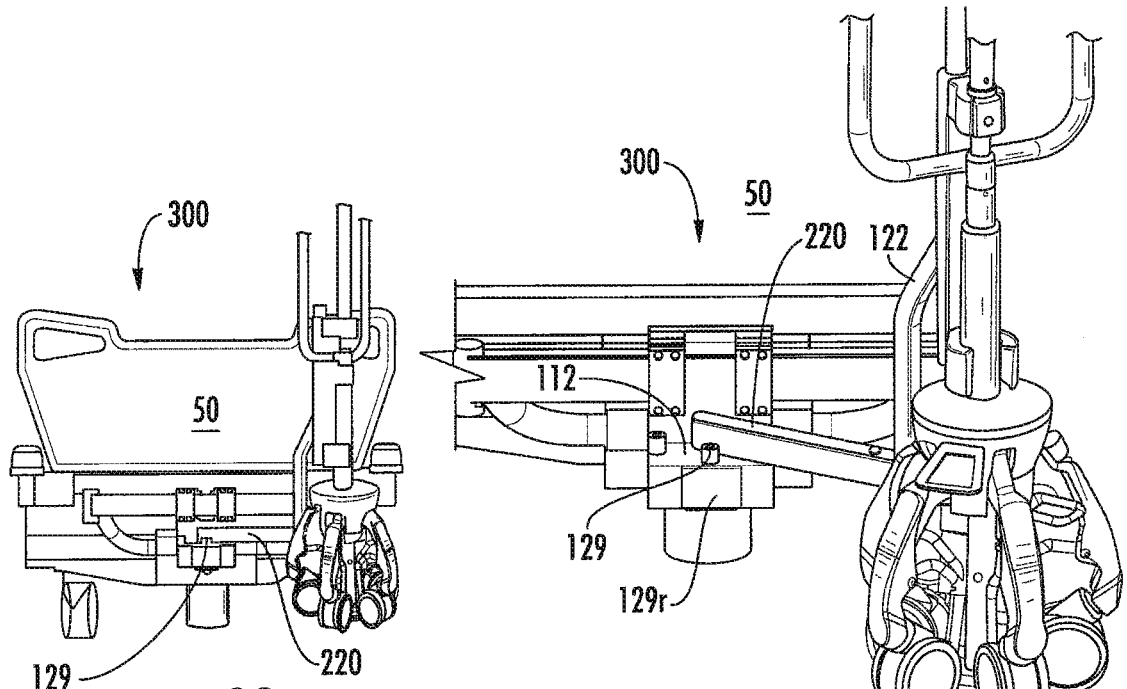
FIG. 9G
FIG. 9H

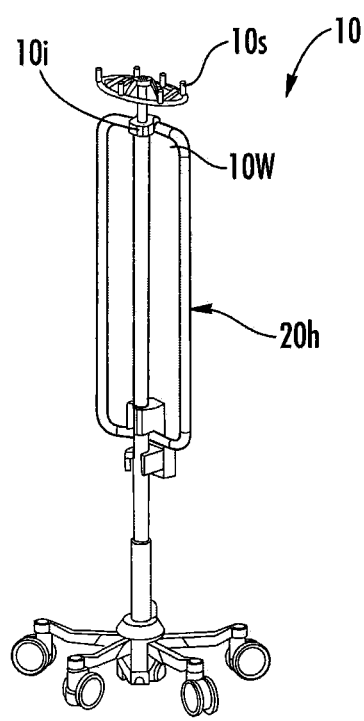
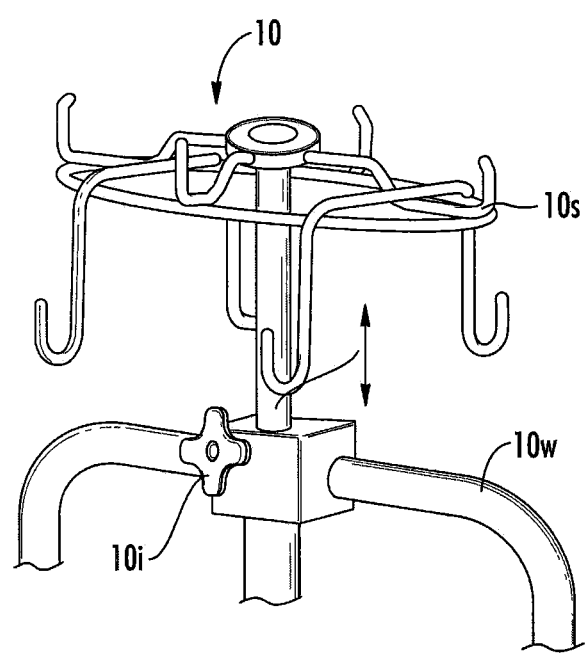
FIG. 11
FIG. 12

DOCKING SYSTEMS FOR MEDICAL DEVICES AND RELATED DEVICES

RELATED APPLICATIONS

This application claims the benefit of and priority to U.S. patent application Ser. No. 15/130,005 filed Apr. 15, 2016 entitled DOCKING SYSTEMS FOR MEDICAL DEVICES AND RELATED DEVICES, which in turn claims the benefit and priority to U.S. Provisional Application Ser. No. 62/148,398 filed Apr. 16, 2015, U.S. Provisional Application Ser. No. 62/207,106 filed Aug. 19, 2015, and U.S. Provisional Application Ser. No. 62/210,724 filed Aug. 27, 2015, the contents of which are hereby incorporated by reference as if recited in full herein.

BACKGROUND

Hospitals and other clinical environments employ accessories used for patients that are oftentimes desired to be moved with a patient. There is a need for docking systems that facilitate one or more of mobility, user access and/or ease of use.

SUMMARY

Embodiments of the invention relate to docking systems for devices that hold accessories, typically in a clinical or hospital environment, for attaching to various devices such as beds, wheelchairs, walkers, wagons, and the like.

The poles can have a plurality of legs which hold wheels, typically casters.

The poles can have wheels that can be small wheels, larger wheels combinations of smaller and larger wheels with or without casters.

In some embodiments, the legs are not retractable but the mast may be extendable/retractable.

In some embodiments, the accessories have docking systems that dock a pole which can be a retractable or a non-retractable pole. The non-retractable pole can have a static floor supported base configuration (although it may have an adjustable height).

In some embodiments, the legs can be moved between an extended configuration where the wheels contact a floor and a retracted configuration where the legs are drawn inward and the wheels are lifted to reside off the floor.

The poles can be configured for various purposes and/or provided as components of various devices. The poles can be an IV pole, an oxygen tank pole, a tray table pole, a monitor support pole, a pole attachable to a pediatric wagon, wheelchair or hospital bed or hospital beds with a pole docking system and/or any combination of the different uses and may be used for other hospital or care-based medical accessories.

Some embodiments are directed to a wheelchair docking system that includes a docking interface attached to a wheelchair for detachably coupling at least one accessory device. The docking interface includes: a base attached to the wheelchair and extending laterally between the right and left side wheels; an upwardly extending support member attached to the base and extending upwardly therefrom; and a pivoting supplemental handle member attached to the upwardly extending support member. The supplemental handle member has a pair of arms spaced apart across a gap space and the supplemental handle member has a first retracted position where the arms are in a vertical or substantially vertical orientation and a second extended position where the arms extend rearward of the back of the wheelchair in a horizontal or substantially horizontal orientation.

The arms of the supplemental handle member can have a length between 6 inches and 36 inches, and the length may optionally be between about 12 inches and 24 inches.

The docking system of the wheelchair can further include a pivoting attachment member held by the upwardly extending support member below the supplemental handle attachment. The pivoting attachment member can include left and right side outwardly extending arms with a respective curved upper surface sized and configured to detachable couple with a respective horizontally extending tubular segment of a respective accessory device.

The system can include a mast attachment member attached to the upwardly extending support member and residing above the supplemental handle attachment. The mast attachment member can be sized and configured to receive a vertically extending tubular segment of a respective accessory device.

The arms of the pivoting supplemental handle member can be laterally separated by a distance between 18 inches and 32 inches.

The pivoting attachment member can be configured to pivot up and down below the supplemental arm.

The system can also include a longitudinally extending spring held between a rear wall of the pivoting attachment member and the upwardly extending support for defining a spring-loaded configuration of the pivoting attachment member.

The system can be in combination with a wheelchair and can include at least one strut attached at one end to the upwardly extending support and at an outer end portion to a tubular frame of the wheelchair.

The docking system and/or wheelchair can be in combination with the accessory device. The accessory device can include a pole with a plurality of wheels.

The pole can be a transformable pole.

Some embodiments are directed to wheelchairs that include a wheelchair body having a back, seat and right and left side wheels and a docking interface attached to the wheelchair for detachably coupling at least one accessory device. The docking interface includes: a base attached to the wheelchair and extending laterally between the right and left side wheels; an upwardly extending support member attached to the base and extending upwardly therefrom; and right and left side longitudinally extending legs extending rearward of the base and having a wheel on a respective outer end thereof for providing stability.

The wheelchair can be in combination with the accessory device. The accessory device can include a pole with a plurality of wheels.

The pole may optionally be a transformable pole.

Yet other embodiments are directed to wagons for pediatric clinical use. The wagons can include a wagon body having a plurality of wheels and a pole docking interface for detachably coupling a pole with wheels.

The pole docking interface can include a hitch attached to a bottom of the wagon body with an outwardly extending end portion comprising a pivoting member with a pair of longitudinally extending arms and a gap space between the arms. The pivoting member can pivot up and down.

The wagon can further include a flat tongue residing under the pivoting member.

The wagon can further include at least one laterally extending attachment member extending at least partially across the gap space between the arms.

The wagon hitch can include a wagon attachment member with a laterally extending channel that receives an axle of a pair of wheels of the wagon.

The wagon attachment member can include at least one downwardly extending channel spaced apart from the laterally extending channel that is sized and configured to allow a fixation member to extend therethrough to affix the attachment member to the wagon.

The wagon can include a laterally extending spring in communication with an inwardly facing end portion of the pivoting member and an adjacent end portion of the attachment member.

The wagon can further include at least one seat in the wagon body for a human child, and wherein the wagon includes a handle extending a distance away from the wagon body in a direction opposing the hitch.

The wagon can further include a laterally extending bar residing at one end of the wagon body a distance above the wagon body, optionally at a height that is between 3 feet and 4 feet tall, to allow a pediatric user to engage the laterally extending bar for pushing the wagon and/or for ambulatory support.

The wagon body can have opposing front and rear ends. The wagon can further include at least one seat in the wagon body for a human child. The wagon can include a handle extending a distance away from the front end of the wagon body. The pole docking interface can include a plurality of outwardly extending pole attachment members extending off the rear end of the wagon body.

The wagon can include a pole attached to the pole docking interface. The pole can include a plurality of legs with wheels. The hitch can releasably engage a single one of the legs.

The wagon can include a pole attached to the pole docking interface. The pole can include a plurality of legs with wheels. At least one leg can have a forward end portion with a recess and a bottom surface. The arms of the hitch can surround one leg with the bottom surface of the leg on the flat tongue of the hitch and the at least one laterally extending attachment member can engage the recess of the leg.

The wagon can include a pole attached to the pole docking interface.

The pole can include a plurality of legs with wheels.

The pole can be a non-retractable (non-transformable) pole with wheels.

The wagon body can hold first and second seats, facing each other.

The wagon can further include at least one pad residing between the pivoting member and a stationary tongue residing under the pivoting front member.

Still other embodiments are directed to hospital beds. The beds can include a docking system attached to the hospital bed. The docking system includes a first arm attached to an end of the bed. The arm can pivot side-to-side relative to the end of the bed. The docking system also includes a bracket attached to the end of the bed at a location residing between 1-3 inches from the floor holding the first arm. The first arm is pivotably attached to extend out from and above the bracket and is configured to pivot at least 30 degrees, side-to-side.

The hospital bed can further include a second arm pivotably attached to the bracket, wherein the bracket is stationary and attached to an end of the hospital bed. The second arm and the first arm can be pivotably attached to the bracket at a common pivot axis and/or joint. The first arm can reside above the second arm and having a different laterally extending length, each with an upwardly extending support. The first and second arms can independently pivot relative to each other about the end of the hospital bed.

The swing arm can pivot between 90-180 degrees.

The hospital bed can include a second swing arm attached to the end of the bed, the second arm can reside above the first arm by between about 0.25-5 inches.

The second arm can be swing arm and the first and second arms can pivot independently of each other, side-to-side, relative to the end of the bed.

The first arm can include a canister bracket.

The second arm can include a pole attachment bracket.

The first arm can be sized and configured to releasably hold an oxygen canister and the second arm can sized and configured to releasably engage a pole with wheels.

The first arm can be shorter or longer than the second arm.

The docking system can include a second arm that can support an upwardly extending member that can include laterally extending pole attachment members that can releasably engage a pole.

The second arm can reside below and can be longer than the first arm.

The first arm can have a length measured from a pivot attachment point on the bracket attached to the end of the hospital bed to an end portion thereof that is between 2 inches to 12 inches.

The hospital bed can include a second arm attached to a bracket held by the end of the bed at a common pivot joint and/or axis on the bracket with the first swing arm.

The first arm can resides a distance above the second arm. The second arm can have a length sufficient to position an upwardly extending member thereof adjacent and behind a canister held by the first arm.

The first (upper) arm can have a length that is different (typically less) than the second (lower) arm.

The second arm can include an upwardly extending pole support member with a curvilinear shape so as to travels upward and laterally outward above the second arm.

The hospital bed can include a second arm attached to the bracket at the end of the hospital bed. The first and second arms can lock together to pivot in concert and unlock to pivot independently of the other.

The hospital bed can be in combination with an oxygen canister held by the first arm and a pole with wheels attached to the second arm.

The pole can optionally be a transformable pole.

Other embodiments are directed to hospital beds with a base arid a docking system. The docking system engages a pole, optionally a transformable pole. The docking system includes a docking base and a curvilinear upright member (optionally attached at a right or left end side of the base of the bed) with at least one pole attachment member facing outwardly therefrom, residing above the base of the hospital bed.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below and/or shown in the accompanying drawings.

BRIEF DESCRIPTION OF THE DRAWINGS

FIG. 2A is a side view of transformable pole releasably holding an oxygen tank and a bed-docking system for the pole according to embodiments of the present invention.

FIG. 2B is a side view of a pressurized tank with a bed docking system according to embodiments of the present invention.

FIG. 6B is a side perspective view of another embodiment of a wagon for cooperating with IV poles according to embodiments of the present invention.

FIGS. 9A-9H are sequential views illustrating exemplary loading/docking steps of a pole according to embodiments of the present invention.

FIG. 11 is a side perspective view of a pole with an IV stand wing for holding fluid bags, infusion pumps and monitors according to embodiments of the present invention.

FIG. 12 is an enlarged view of a top portion of the pole shown in FIG. 11.

DETAILED DESCRIPTION

Figure 1A:
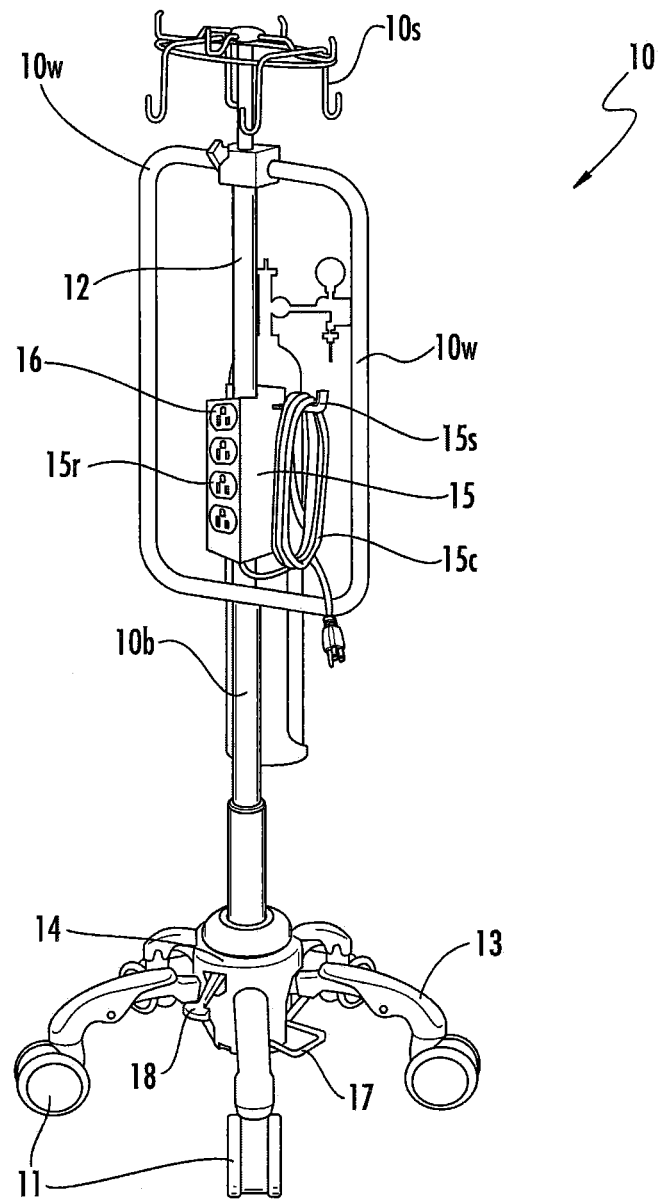
FIG. 1A is a perspective view of a transformable pole which comprises a power strip unit and an oxygen tank holder according to embodiments of the present invention.

The present invention now will be described more fully hereinafter with reference to the accompanying drawings, in which illustrative embodiments of the invention are shown. Like numbers refer to like elements and different embodiments of like elements can be designated using a different number of superscript indicator apostrophes (e.g., 90', 90", 90'").

In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art. The term "Fig." (whether in all capital letters or not) is used interchangeably with the word "Figure" as an abbreviation thereof in the specification and drawings. In the figures, certain layers, components or features may be exaggerated for clarity, and broken lines illustrate optional features or operations unless specified otherwise. In addition, the sequence of operations (or steps) is not limited to the order presented in the claims unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "bottom", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass orientations of above, below and behind. The device may be otherwise oriented (rotated 90° or at other orientations) and the spatially relative descriptors used herein interpreted accordingly.

The term "about" refers to numbers in a range of +/−20% of the noted value. The term "substantially" means that the configuration can vary somewhat, such as "substantially horizontal" and "substantially vertical" means that the member can reside at +/−15 degrees from horizontal or vertical, respectively.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

The terms "accessory" and "accessory devices" refer to any clinical or hospital device that may be desirable to be provided for and/or moved with a patient including poles such as IV poles, monitor supports, tables, trays, pump supports, oxygen tank/canisters and the like.

Figure 1B:
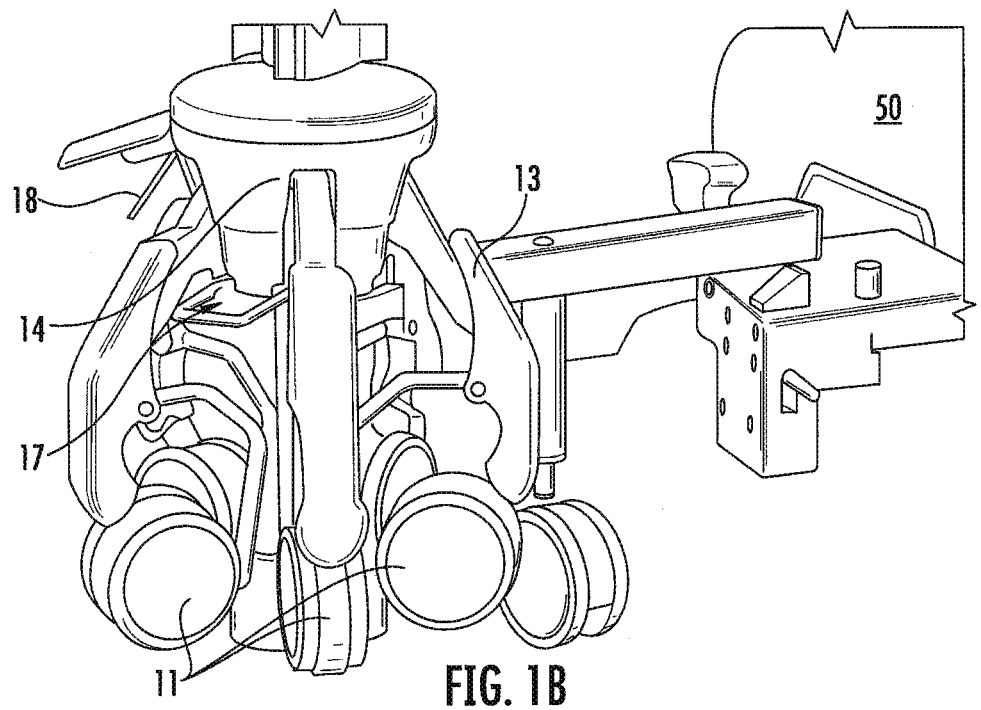
FIGS. 1B and 1C are enlarged views of retracted/stowed configuration and an extended operational configuration, respectively, of the transformable pole shown in FIG. 1A according to embodiments of the present invention.
Figure 1C:
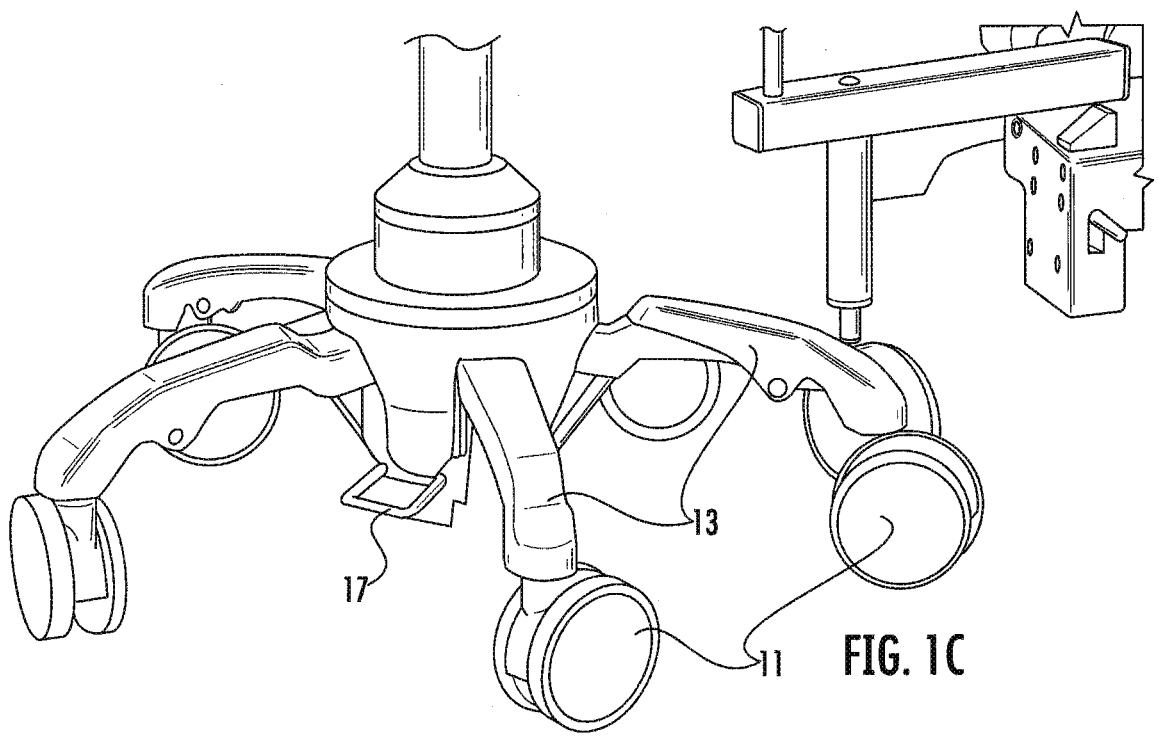

Turning now to the figures, FIG. 1A illustrates a pole 10 with an onboard power strip unit 15 and tank holder 22 for a pressurized gas tank 20, such as an oxygen tank 20. The pole 10 can optionally be a transformable pole. The term "transformable" when referring to some embodiments of the pole 10 means that the pole 10 can transform between at least two different configurations, typically including a stowed configuration with the wheels 11 off of/above a support floor as shown in FIG. 1B and an extended configuration with the wheels 11 on the floor as shown in FIG. 1C with the wheels 11 able to provide a weight bearing support for the pole 10. However, in some embodiments, the pole 10 can be a non-transformable (i.e., non-retractable) pole so as to have a static extended mobile configuration with its rollers/casters on the floor.

The pole 10 can include a lift mechanism 14 held by the mast 12. The lift mechanism 14 can slide up and down relative to a lower end portion of the pole 12. The lift mechanism 14 holds legs that are attached to the wheels 11. The legs 13 can pivot inward and outward relative to the mast 12 to be able to retract and extend the wheels 11 in the stowed and extended positions, respectively. The pole 10 can include at least one foot lever 17 for moving between the stowed and extended positions. As shown, the pole 10 has a manually-actuated foot lever 18 in communication with the lift mechanism 14 for engaging an onboard (e.g., gas spring) actuator that raises the wheels 11. The pole 10 may also have a second lever 17 for lowering the wheels 11. The second lever 17 can manually lower the wheels from force applied to the second lever 17. In some embodiments, the wheels 11 are caster-type wheels capable of freely rotating along a leg-wheel connection. Although in this particular depiction there are five legs 13 with five four-inch caster-type wheels 11, embodiments with different numbers of legs (such as 1, 2, 3 or 6 or more) and different sized or types of wheels, or combinations of different types or sizes, larger or smaller or combinations of different size wheels may be used.

The lift mechanism 14 may include a gas spring as described in U.S. Pat. No. 7,918,422, the contents of which are hereby incorporated by reference as if recited in full herein. Alternatively, other lift mechanisms 14 including, for example, electric motor or pneumatic driven gears and/or links may be used.

As shown in FIG. 1A, the pole 10 includes an upwardly extending mast 12 that can be configured to hold the power strip unit 15 with electrical (plug-in) receptacles 15*r* and an optional power cord 15*c*. The power strip unit 15 can include an onboard surge protector. The power cord 15*c* can be configured as a retractable power cord in a support or may be a loose length of cable that can be held about a cord support 15*s* on the mast 12 and/or on the body of the power strip unit 15. The pole 10 can also hold wings 10*w* under a suspension support 10s for suspending bags of fluids for patient administration, such as IV fluids and the like. The wings 10w can support patient monitors and/or other devices. See, e.g., U.S. Pat. Nos. 7,497,407; 7,918,422; 7,735,789; and US Patent Application Publication 2013/0181100, the contents of which are hereby incorporated by reference as if recited in full herein.

As also shown in FIG. 1A, the power strip unit 10 can have an oxygen tank holder 20h. The oxygen tank holder 20h can comprise oxygen tank shell 22 that can hold the oxygen tank to the pole 10. The oxygen tank shell 22 can be integral with the power strip unit 15 as shown or may be a separate component. The oxygen tank shell 22 can have a length that is at least 50% of the length of the oxygen tank 20 and can releasably receive a lower end of the oxygen tank 20. The power strip unit 15 can be integrally affixed to the mast of pole 12 or may be releasably attachable to the mast of the pole 12. The power strip unit 15 can comprise at least one clamp 16 so as to be a clamp-on unit 15 that allows the unit 15 to be removed for cleaning, repair or replacement, and the like. Although the power strip unit 15 is shown with four separate electrical receptacles, it may include a single receptacle or more than four. Also, the power strip unit 15 can orient the receptacles 15r in different directions or the unit 15 can have at least one that faces a different direction than another, e.g., one that faces the front, one that faces the back, one that faces a side or wing 10w, and the like. The power strip 15 can have rotatable receptacles for altering orientation or may have a fixed receptacle orientation.

Referring to FIG. 2A, the pole 10 can be a dedicated oxygen tank holder 20h. Although shown as having the wheels 11 and legs 13, other pole configurations may be used not requiring a transformable pole configuration or using a different transformable pole configuration. For example, the pole 10 can comprise fewer legs 13 and wheels 11 than shown, e.g., three or four wheels 11. The pole 10 can have smaller wheels 11 and/or casters such as one or more having a two-inch, three-inch or under four inch diameter. The pole 10 can have a different lift mechanism 14 and different levers configurations 17, 18. The pole 10, when a transformable pole, can be configured to have a smaller extended perimeter floor "footprint".

Still referring to FIG. 2A, the pole 10 can include a plurality of vertically spaced apart support members 23, 24 that can releasably engage a respective oxygen tank 20. The pole 10 can attach to a hospital bed 50 via a bed docking system 110. In some embodiments, the bed docking system 110 can include a plurality of laterally extending support arms 114, 116 that can releasably engage the mast 12 of the pole 10. The pole 10 can dock to the bed 50 so that the arms of the docking system 114, 116 alternate with those of the pole 23, 24. The support members 23, 24 face outwardly and allow a user to change out the oxygen tank 20 when docked to the bed 50. The docking system 110 can include a base 112 that is secured to a base or frame 50b of the hospital bed, typically closer to a head board or end. The base 112 can have a curvilinear upwardly extending support bracket 113 that holds the arms 114, 116 so that the arms are parallel, one above another and extend out from an end or a side of the bed 50 a short distance so as to have a compact on-board configuration. Typically, the arms extend out from a profile or perimeter of the bed between about 2-10 inches relative to one or more of the base 50b, or side rail 50r, or headboard 50h. A user can slide the pole to engage the arms 114,116 and lock the pole 10 to the docking system 110, then raise the legs 13 to raise the wheels 11 off the ground and lock the tank holder into the docking system 110, supported by the bed 50.

Figure 2C:
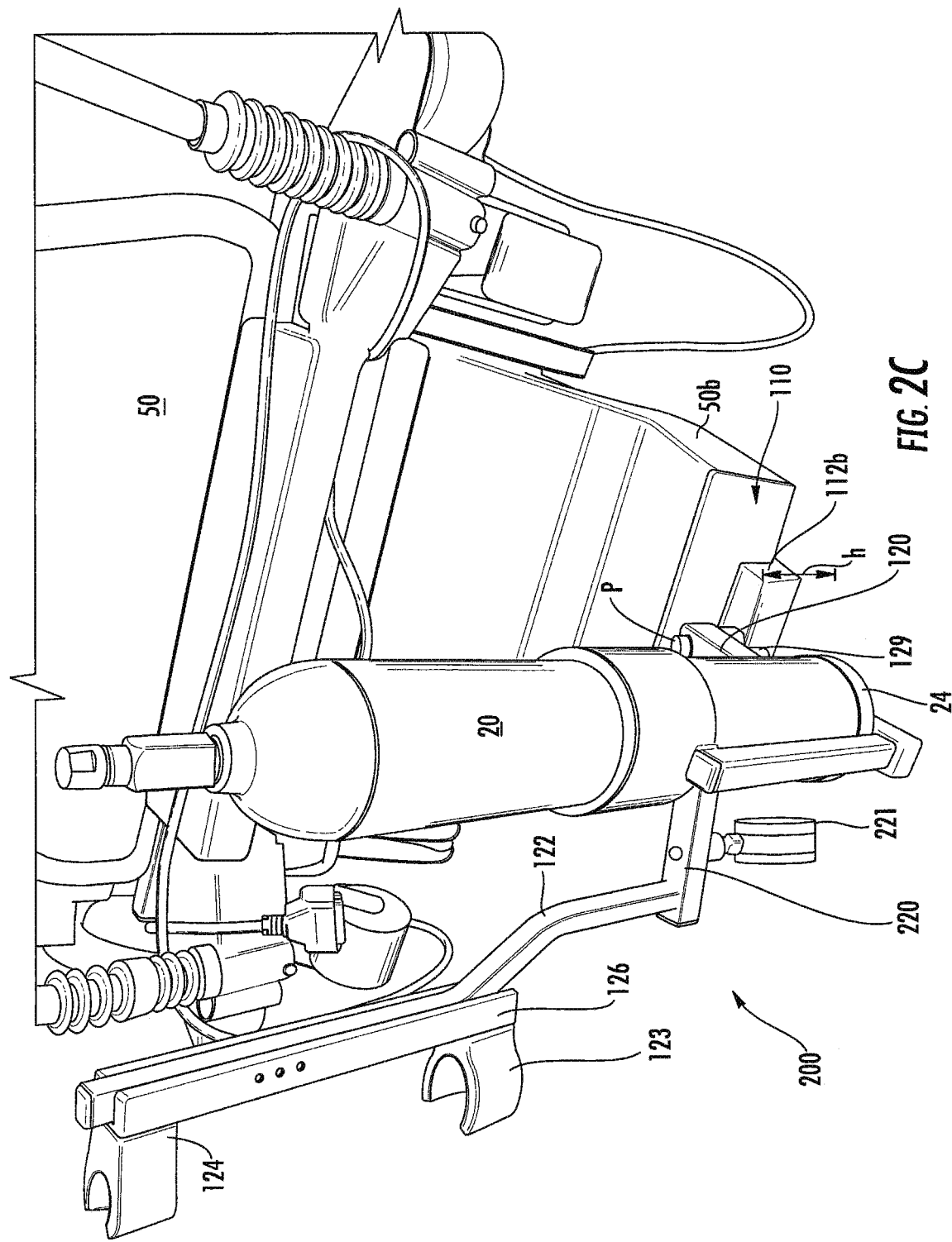
FIG. 2C is a top perspective view of a pressurized tank adapter with a bed docking system according to embodiments of the present invention.
Figure 2D:
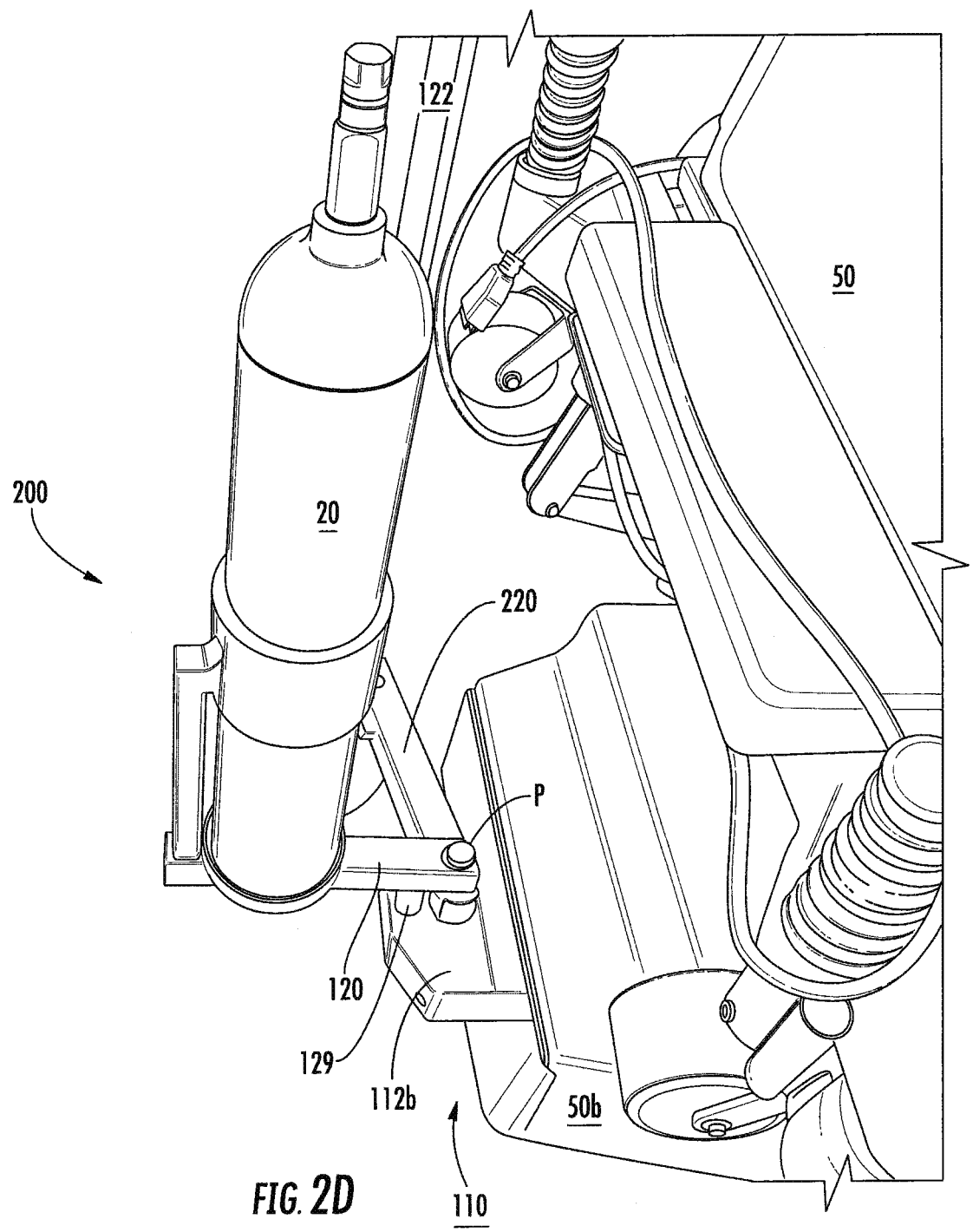
FIG. 2D is a top, side perspective view of the pressurized tank adapter and bed docking system shown in FIG. 2C.

FIGS. 2B-2D illustrate another embodiment of a bed adaptor assembly 200 with a tank holder 20h. In this embodiment, the assembly 200 includes a first (i.e., swing) arm 120 for holding a compressed gas tank 20. The first arm 120 can rotate and/or pivot side-to-side when mounted to an end or outer perimeter of the bed 50. The first arm 120 can pivot at least between 30-60 degrees, typically between 30-180 degrees, more typically between about 90 degrees to about 180 degrees, and preferably about 180 degrees, when attached to the bed 50. The first (swing) arm 120 can comprise a bed docking system 110 with a base 112 that is attached to a bottom portion and/or a base of the end of the bed 50b.

In some embodiments, and as shown, the assembly 200 can also include a second arm 220 for holding a pole attachment member 240 for releasably engaging the pole 10. The second arm 220 can include at least one wheel and/or caster that can contact a floor. Where the second arm 220 is used, the first arm 120 can rotate/pivot independent of the second arm 220. The first arm 120 and the second arm 220 can optionally each pivot side-to-side when docked to a bed 50, typically by between 90-180 degrees. The first and second arms 120, 220 can both be attached to the bed docking system 110 with the base 112 that is attached to a bottom portion and/or a base of the bed 50b. The first swing arm 120 can support the tank 20 using any suitable attachment/support members such as, but not limited to, sleeves, rings, arms, cups, braces or other tank attachment members, shown as upper and lower attachment members 23, 24. The first arm 120 can be shorter and reside above the second arm 220. The pole 10 can support various devices such as monitors, IV bags, pumps and the like for transport with the tank 10 when a bed 50 is moved. Thus, all pole mounted devices can be easily transported with the tank 20.

The second arm 220 may not pivot relative to the first swing arm and/or the bed 50. The second arm 220 may be a swing arm and can pivot with or independent of the first swing arm 120.

In some embodiments, the first and second arms 120, 220 can each be attached via a single pivot axis or joint at pivot location P to a bracket 112b, which may be a planar horizontal upper surface of a bracket 112b, of the docking base 112. The bracket 112b may extend outwardly from the bed frame a distance to place the pivot P at a distance of 0.25-2 inches on the bracket in some embodiments. The bracket 112b can be attached to the end of the bed to reside at a height that is between about 1-3 inches above the floor. A stop member 129 may be held by the bracket 112b at a location that blocks the second swing arm 220 from pivoting past this member. This stop member 129 can also or alternatively be configured as a release member that allows the second arm 220 to pivot a further distance (FIG. 2D, FIG. 9H). For easier transport, the second arm 220 can be oriented to place the arm to the right of left of the rear of the bed and the release button 129 can prevent the arm from moving during transport.

The second arm 220 can support an upwardly extending member 122 that can include laterally extending pole attachment members 123, 124 that can releasably engage pole 10.

The second arm 220 can reside below and can be longer than the first arm 120. The first arm 120 can have a length measured from the pivot axis and/or attachment P to the perimeter of the lower attachment member 24 that is between 2 inches to 12 inches. The first arm 120 can reside adjacent but a distance above the second arm 220, typically by about 0.25 inches to about 5 inches, more typically between about 1-3 inches.

The second arm 220 can have a length sufficient to position the upwardly extending member 122 adjacent, and in behind the tank 20 and/or a perimeter of the stroke radius of the first swing arm 120, typically spaced apart from the bed 50 a further distance than the tank 20. When the first and second arms 120, 220 are aligned, one above the other, at least a lower portion of the member 122 can reside between 0.25 inches and 3 inches of the tank 20 held by the first swing arm 120.

In some embodiments, as shown in FIGS. 2C and 2D, the upwardly extending pole-support member 122 can have a curvilinear shape so as to bend or extend outward a distance relative to a lower portion attached to the second arm 220, as it travels up above the arm 220. In other embodiments, the pole support member 122 can have other shapes and/or configurations and may be vertically straight as shown in FIG. 2B, for example.

The first and second arms 120, 220 can lock together to pivot in concert. The first and second arms 120, 220 can include one or more locks to lock into a desired orientation with respect to the bed 50 for transport or use.

As shown in FIGS. 2C and 2D, the pole support member 122 can hold a bracket 126 that holds the pole support members 123, 124. The bracket 126 can be slidably attached to the pole support member 122 for height adjustment by a user or be fixedly attached at a desired height such as at an OEM facility (original equipment manufacturer).

Figure 3:
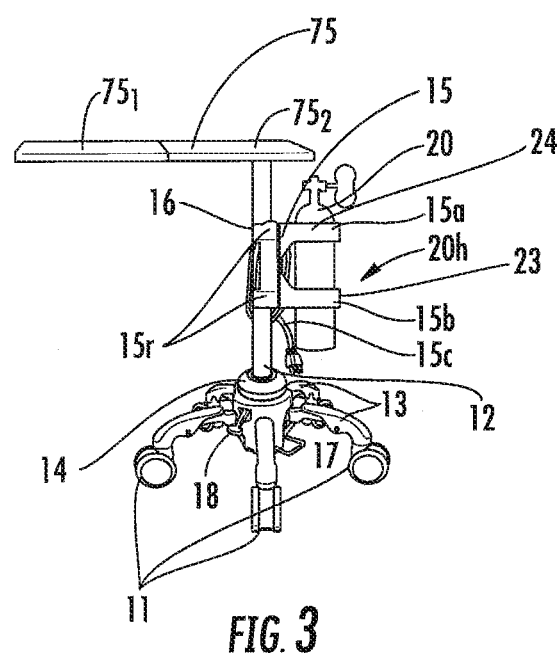
FIG. 3 is a side perspective view of a tray table with a transformable pole, power strip unit and oxygen holder according to embodiments of the present invention.

Referring to FIG. 3, the pole 10 can be configured as a multi-purpose pole 10 with a power strip unit 15, a tray table 75 and an oxygen tank holder 20h. As described with respect to FIGS. 2A, 2B above, the pole 10 can have a different configuration than shown, including a different transformable pole configuration with different numbers of wheels/casters, different size wheels/casters and a different lift and/or wheel-extend lever and mechanism. The pole 10 can include a plurality of vertically spaced apart support arms 23, 24 that can releasably engage a respective oxygen tank 20. The arms 23, 24 can extend off the power strip unit 15 so that the power strip unit 15 has integral oxygen tank support arms 15a, 15b. The power strip unit 15 can comprise at least one laterally extending arm or clamp 16 that attaches to the mast 12 of the pole. The tray table 75 can include foldable segments $75_1$, $75_2$. The pole 10 can attach to a hospital bed 50 via a bed docking system 110 such as that shown in FIG. 2A or 2B, for example.

Figure 4A:
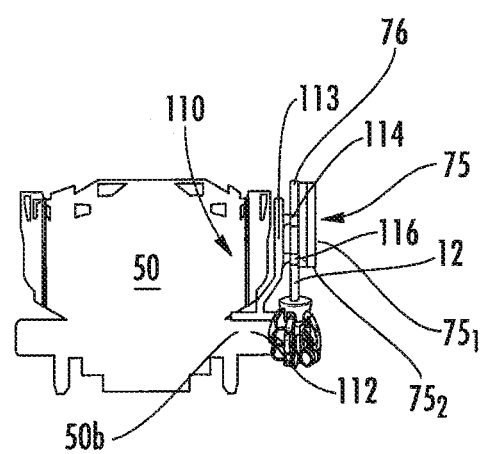
FIG. 4A is side perspective view of a tray table and transformable pole, with the pole in a retracted configuration, and the table in a stow configuration, with the pole docked to a bed mount on a hospital bed according to embodiments of the present invention.

Referring to FIG. 4A, the pole 10 can be docked to the hospital bed 50 via the docking system 110 while the tray table 75 is in a compact stowed position with the table top surfaces $75_1$, $75_2$ residing adjacent and parallel to each other and extending vertically. As shown, the pole 10 and table 75 may be used without the oxygen tank holder 20h. The pole 10 can have a pivot attachment 76 to the tray table 75. The two tray surfaces may also be pivotably attached for compact storage. A user can configure the tray 75 to expose one tray table surface for use (with the other held under the outer surface) or expose both surfaces. While a pair of table top surface panels are shown, one or more than two panels may be used. One or more of the table top surface panels $75_1$, $75_2$ may be telescopically mounted to allow for longer/shorter use orientations (not shown). Again, as described with respect to FIG. 2A and FIG. 3 above, the pole 10 can have a different configuration than shown, including a different transformable pole configuration with different numbers of wheels/casters, different size wheels/casters and a different lift and/or wheel-extend lever and mechanism.

Figure 4B:
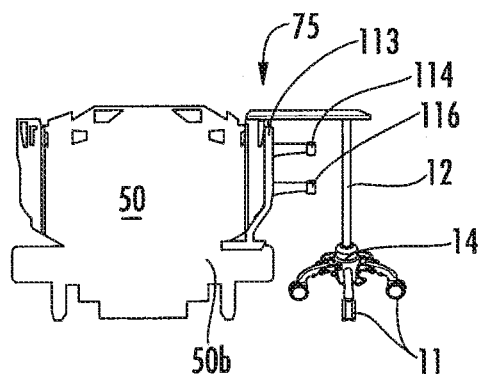
FIG. 4B is a side perspective view of the tray table and pole shown in FIG. 4A illustrating the table in one use configuration extended laterally outward away from the bed and the pole in the extended configuration and undocked from the bed according to embodiments of the present invention.
Figure 4C:
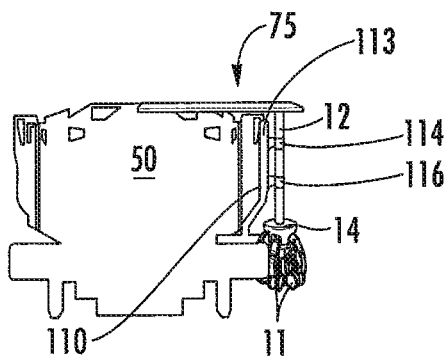
FIG. 4C is a side perspective view of the tray table and pole shown in FIG. 4B, illustrating the pole in a retracted configuration and docked to the bed mount with the tray table in an open position according to embodiments of the present invention.

FIG. 4B shows that the pole can be releasably attached to the docking system 110 allowing the pole 10 to be slid outward away from the bed 50 on extended wheels 11 with the tray table 75 opened with both tray top surfaces $75_1$, $75_2$ horizontal and residing between the bed 50 and the pole 10. FIG. 4C shows the pole 10 docked to the bed docking system 110 and the wheels 11 raised off the floor. The tray 75 can also be opened to expose one or both tray top surfaces when docked to the bed.

Figure 5A:
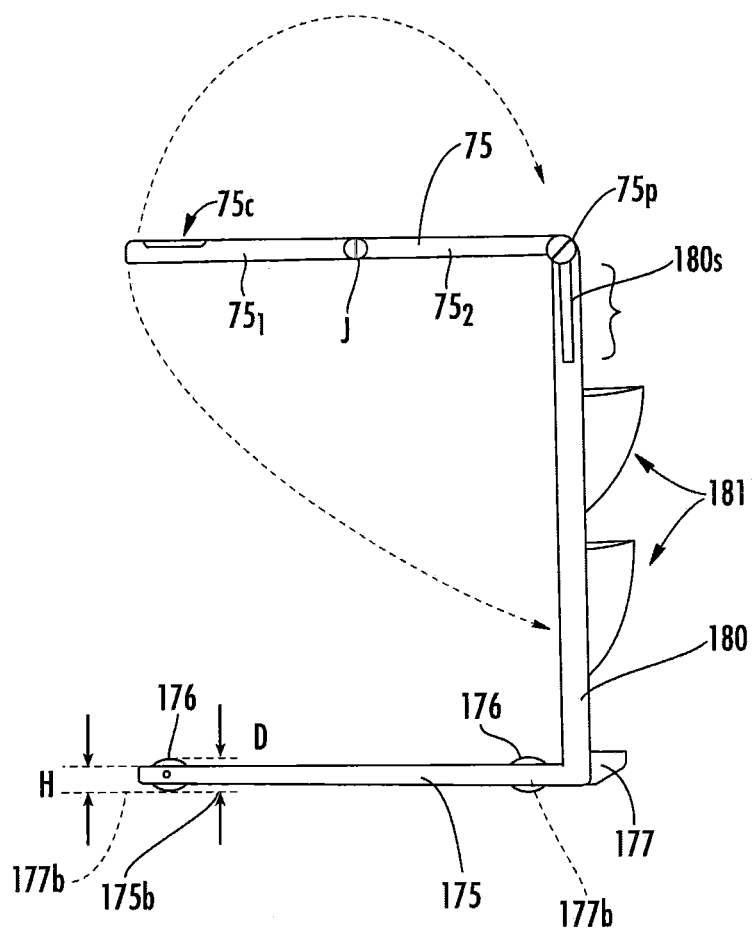
FIG. 5A is a side view of a tray table assembly that can be used with hospital beds according to embodiments of the present invention.

FIG. 5A shows another embodiment of a tray table 75'. In this embodiment, the tray table 75' has first and second tray top surfaces/members $75_1$, $75_2$ that are foldable and can be supported by a low profile base 175 that can include a plurality of wheels/casters 176. The term "low profile" means that the base 175 with wheels/casters 176 can have a maximum height distance "D" above the floor that is under 1 inch, typically between 0.5 inches and 0.9 inches. The low profile base 175 can have a vertically extending height/thickness that is between 0.25 inches 1 inch. A bottom of the base 175b can reside within 0.1 inches and 0.5 inches of the floor. The centerlines of the axis of rotation A of the wheels/casters 176 can be at a height H that is no more than 1 inch above the floor, are is typically within about 0.25 inches and 0.6 inches of the floor.

The table top 75' can have a joint between the two table top members $75_1$, 752 and the second table top member $75_2$ can be pivotably attached to the vertical support member 180 at pivot 75j. The pivot attachment 75j can reside in a slot in the vertical support member 180 to allow for vertical height adjustment of the table top. The entire tray top, i.e., both first and second members $75_1$, $75_2$ in their flat (fully extended) orientation can pivot down against the support member 180 or the first table member can pivot up over the second table top member 75 as indicated by the two arrow heads and the associated broken lines in FIG. 5A.

The tray table 75' can optionally include a foot lever 177 in communication with one or more wheel locks or brakes 177b that can engage one or more of the wheels 176. The wheels 176 can each have a lock or brake 177b. Where used, a manually operated foot actuation lever 177 can engage the one or more locks or brakes 177b.

The first table top member $75_1$ can have a free end an optional cup holder 75c that can extend over a user/patient in a hospital bed. The vertical support member 180 can optionally hold storage containers 181 such as bins, sleeves or bags.

The low profile base 175 can allow the tray table 75' to be a universal tray table that can fit under most (at least 75% of hospital beds in a particular facility), if not all, commercially available hospital beds on the market today and/or used with different hospital beds from different manufacturers.

Figure 5B:
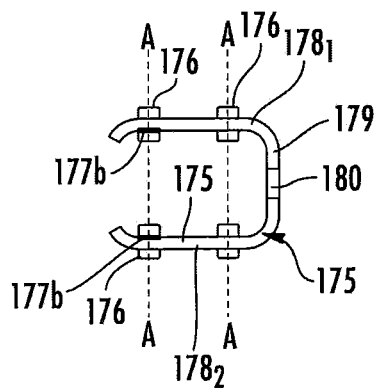
FIG. 5B is a top view of the tray table assembly, shown without the table top according to embodiments of the present invention.
Figure 6A:
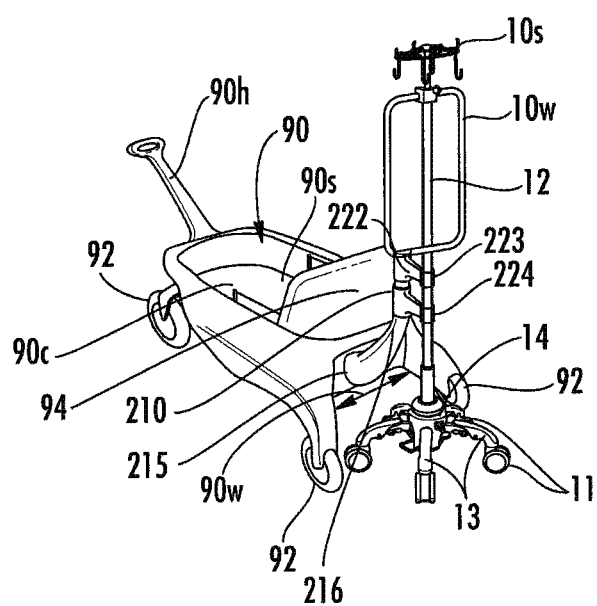
FIG. 6A is a side perspective view of a wagon with a wagon docking mount and an engaged pole according to embodiments of the present invention.

As shown in FIG. 5B, the low profile base 175 can have first and second legs $178_1$, $178_2$ attached by a laterally extending spanning segment 179 to provide structural support for the tray table members $75_1$, $75_2$. The legs $178_1$, $178_2$ can have a length that is about the same or greater than a length of the table top when in a fully extending (unfolded) configuration. The length can be between about 18 inches to about 4 feet. The legs $178_1$, $178_2$ can be spaced apart from each other by between about 2-4 feet. The legs $178_1$, $178_2$ may be curvilinear. FIG. 6A illustrates a pole 10 cooperating with a pediatric wagon 90. The wagon 90 can include a pole docking system 210 that includes at least one pole attachment member 222, shown as vertically spaced apart members 223, 224. Where more than one pole attachment member 222 is used, the pole attachment members may be stationary or may rotate side to side. The at least one pole attachment member 222, e.g., the members 223, 224 may be telescopically configured to allow for adjustment in position relative to the wagon 90 (closer or further away).

The wagon 90 can include a child seating space 90s which may have an integral or attachable chair or cavity. The wagon 90 can include a handle 90h. The wagon 90 can have at least one front wheel 92 and least two spaced apart rear wheels 92 proximate the pole docking system 210 which are spaced apart a distance 90w. A plurality of legs 13 may extend between the rear wheels 92. Once locked to the docking system 210, the legs 13 can optionally be retracted and the wheels 11 lifted off the floor.

The wagon 90 can include a back 94 that rises above the cavity 90c. The wagon can be attached to hold the docking system 210. The back 94 can taper outwardly as it rises above the cavity 90c. The docking system 210 can include a lower brace 215 that holds a curvilinear upwardly extending bracket 216. The pole attachment member 22 can be held by the bracket 216 extending out from the back 94 of the wagon 90. The wagon 90 can be provide in different colors or custom colors and/or with whimsical decorations, logos, pictures or images to be more appealing to pediatric users. As described with respect to FIGS. 2A, 3 and 4A above, the pole 10 can have a different configuration than shown and is not required to be a transformable pole. Where the pole is a transformable pole, it can have a different transformable pole configuration with different numbers of wheels/casters, different size wheels/casters and a different lift and/or wheel-extend lever and mechanism.

The wagon 90 may have rails 90r (FIG. 6B) such as side rails that can be raised/lowered, removed or be stationary, or otherwise translated relative to the cavity of the wagon body. The wagon 90 may include safety restraints such as seat or lap belts and the like.

FIG. 6B illustrates another embodiment of a pediatric wagon 90'. In this embodiment, the wagon 90' can include a handrail 190 that extends off an end portion of the wagon 90'. A patient/user can use the handrail 90r for support to promote ambulation/physical therapy. The patient/user can also or alternatively ride inside the cavity 90c of the wagon 90'. The pole 10 may dock (e.g., clamp) to the wagon and a user/patient can pull the pole along as he/she pushes the wagon. Alternatively, another user may pull the pole separately as a patient/user pushes the wagon 90'. The pole 10 may be provided with different width wings, W1, W2, as shown.

The handrail 190 can reside at a height above a patient's waist and below a patient's shoulders. The handrail 190 can be height adjustable. In some embodiments, the wagon can include a pair of spaced apart struts 191 that extend above the wagon bed 90c and hold the handrail 190. The struts 191 can include downwardly extending slots 192 that allow for the handrail 190 to be positioned at different heights. In some embodiments, the wagon 90' may include a plurality of handrails positioned at different heights so that a user can use the handrail at the appropriate height (not shown).

The wagon 90' can include a bumper and/or rounded forward edge 193 to provide a cushion against collision or contact with another object.

FIGS. 13A-13D and 15A-15H illustrate another embodiment of a wagon 90". The wagon 90" can include a docking system 210 provided as a hitch 210h. While the hitch 210h' may be particularly suitable for engaging an elongate pole 10 with legs 13 over wheels 11, it may be useful to engage other accessories and/or devices, particularly moveable devices and particularly for ambulatory uses in clinical and/or hospital settings.

Referring to FIGS. 13A-13D and FIGS. 14A-14D, the hitch 210h can have one outwardly facing end portion forming the pole/hitch interface $210h_1$ (e.g., "latch") and an inwardly residing end portion (FIG. 14A) defining the wagon/hitch interface $210h_2$. The wagon 90" can have a cavity 90c and one or more seats 90s. The wagon 90" can have a plurality, typically four, wheels 92. The wagon 90" and wheels 92 may comprise molded plastic or polymeric material. The wagon 90" can have laterally extending axles 192 (FIG. 13B) holding the wheels 92, typically one axle 192 for the front wheel pair (the wheel pair adjacent/facing the handle 90h) and one axle 192 for the back wheel pair).

Figure 13A:
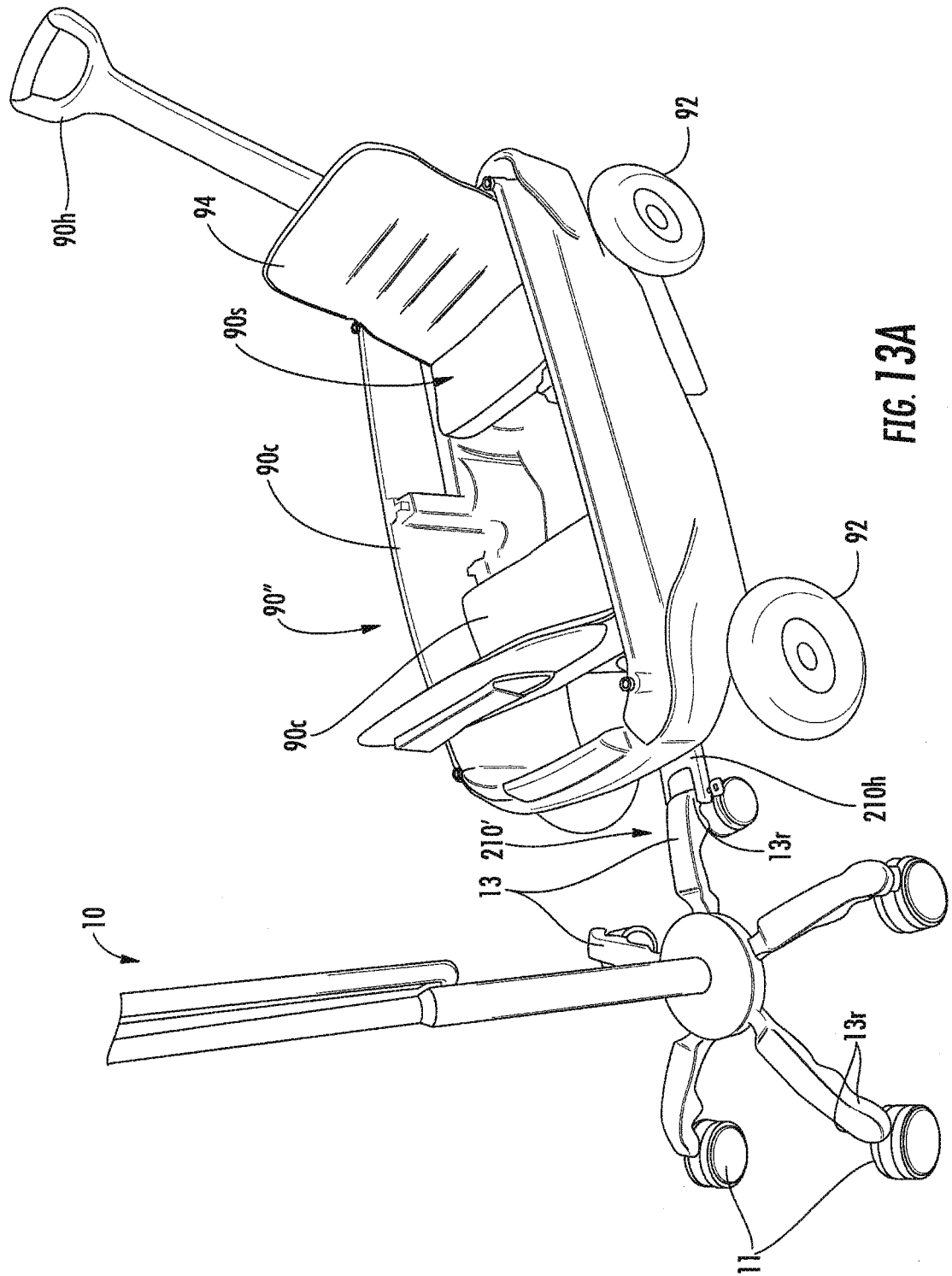
FIG. 13A is a side perspective view of another embodiment of a pediatric wagon with a pole interface according to embodiments of the present invention.
Figure 13B:
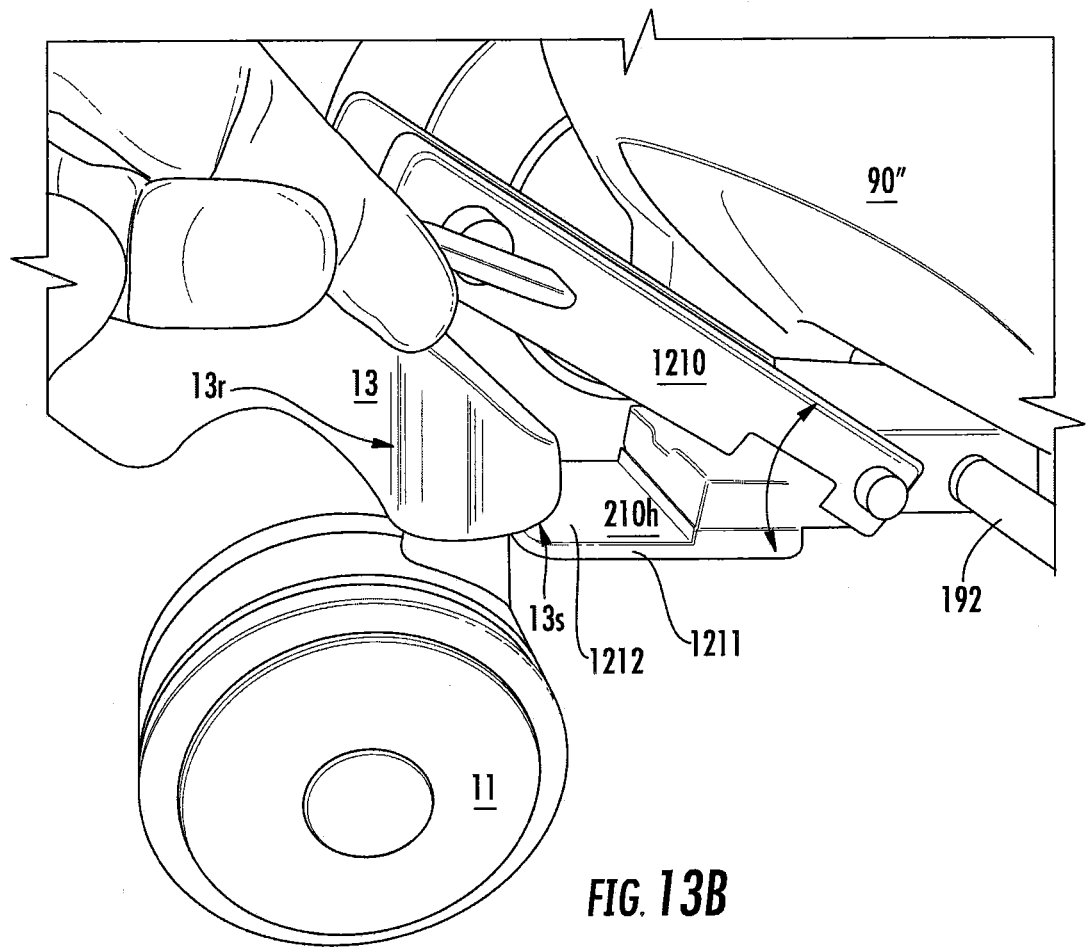
FIG. 13B is a side view of the wagon with the attachment interface according to embodiments of the present invention.
Figure 13C:
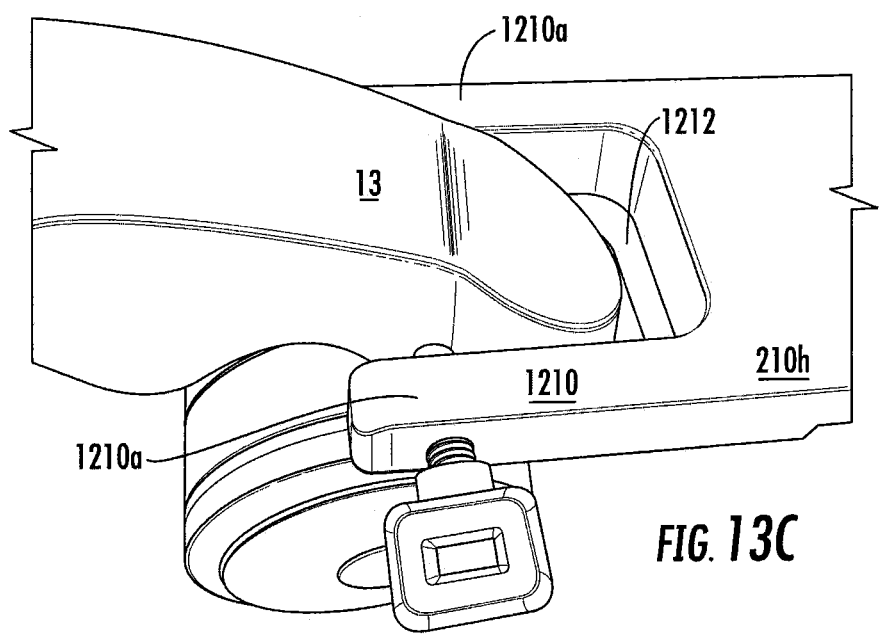
FIG. 13C is an enlarged, top, side perspective view of the hitch/pole interface according to embodiments of the present invention.

Although shown as four wheels 92 in FIGS. 6A, 6B and 13A, more than four wheels 92, such as six or more wheels may be used or it may be possible to use three wheels. The wheels 92 can be of the same or different sizes (diameters and/or widths).

Referring again to FIGS. 13A-13D and FIGS. 14A-14D, the hitch 210h can have a first member 1210 that pivots down about pivot joint J to engage a recessed segment 13r of a single leg 13 of the pole 10 and pivots up to release the leg 11. The recessed segment 13r can be defined by transition rearward toward the pole from a curvature of the leg 13 associated with a portion of the leg that extends down about a vertically extending shaft of a wheel/caster 11. The pivoting member 1210 can hold at least one laterally extending attachment member 1214 that can engage the recessed segment/region 13r of the leg 13. The members 1214 can be laterally adjustable or be fixed in position. Where two attachment members 1214 are used, the members 1214 can face each other across the arms 1210a and can reside spaced apart a distance (they are not required to contact each other).

Figure 13D:
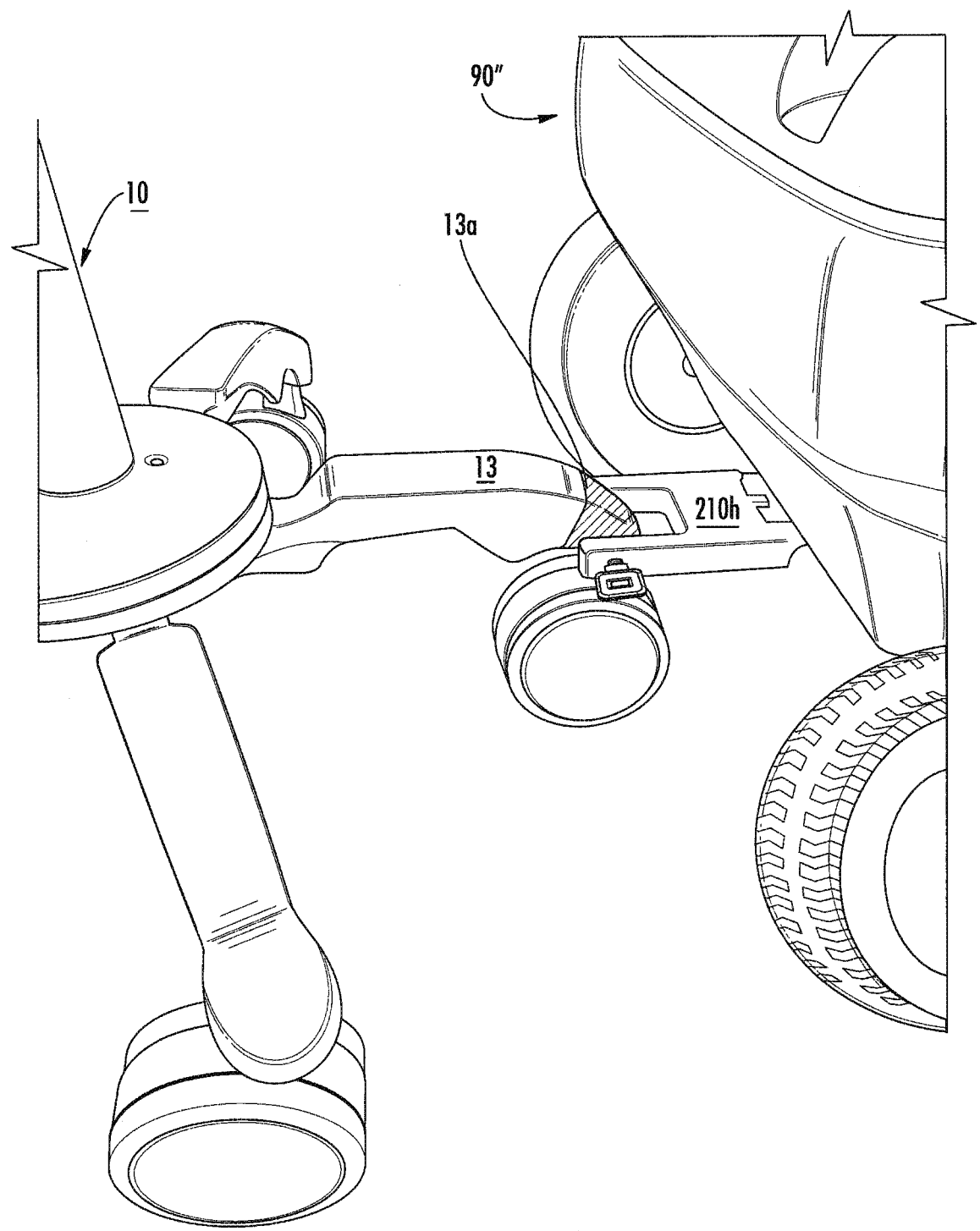
FIG. 13D is a side perspective view of the pole attached to the hitch of the wagon according to embodiments of the present invention.

The leg 13 can be a standard leg of an accessory pole, e.g., IV pole and all legs 13 may have the same configuration as shown although only one attaches to the hitch 201h. In some embodiments, the leg 13 for securing to the hitch 210h may have a unique leading end shape from the other legs and/or may include a leg adaptor 13a (FIG. 13D). The leg adaptor 13a can comprise an elastomeric sleeve, a molded overcoat and/or shaped feature or member for providing a desired interface/connection, for example.

Figure 15B:
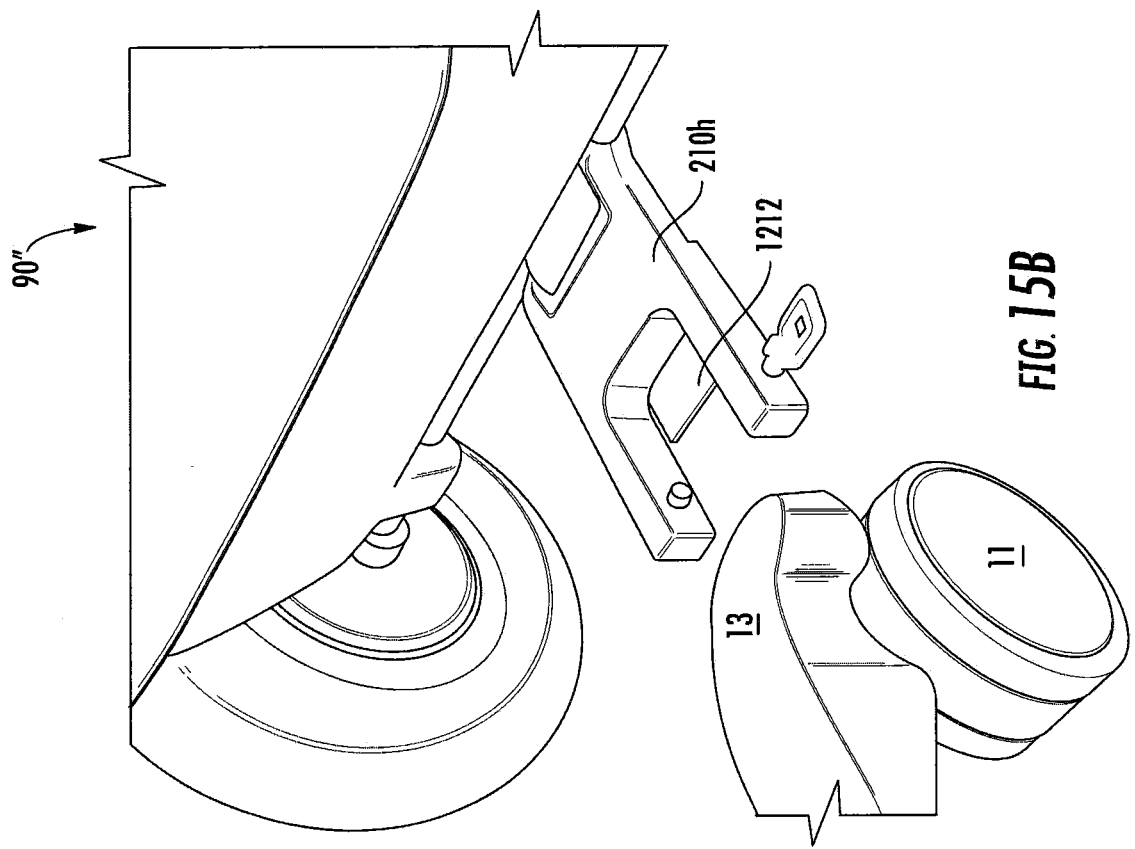
FIGS. 15A-15H are screen shots of a video illustrating exemplary sequences of docking/using and releasing the pole/wagon shown in FIGS. 13A-13D according to embodiments of the present invention.
Figure 15A:
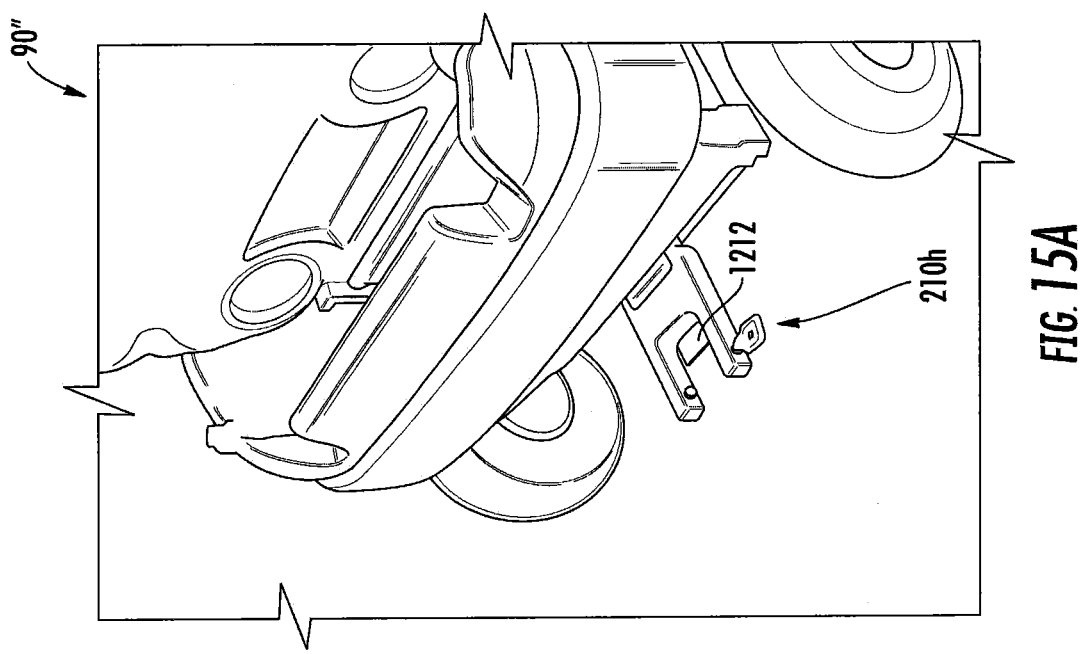
Figure 15C:
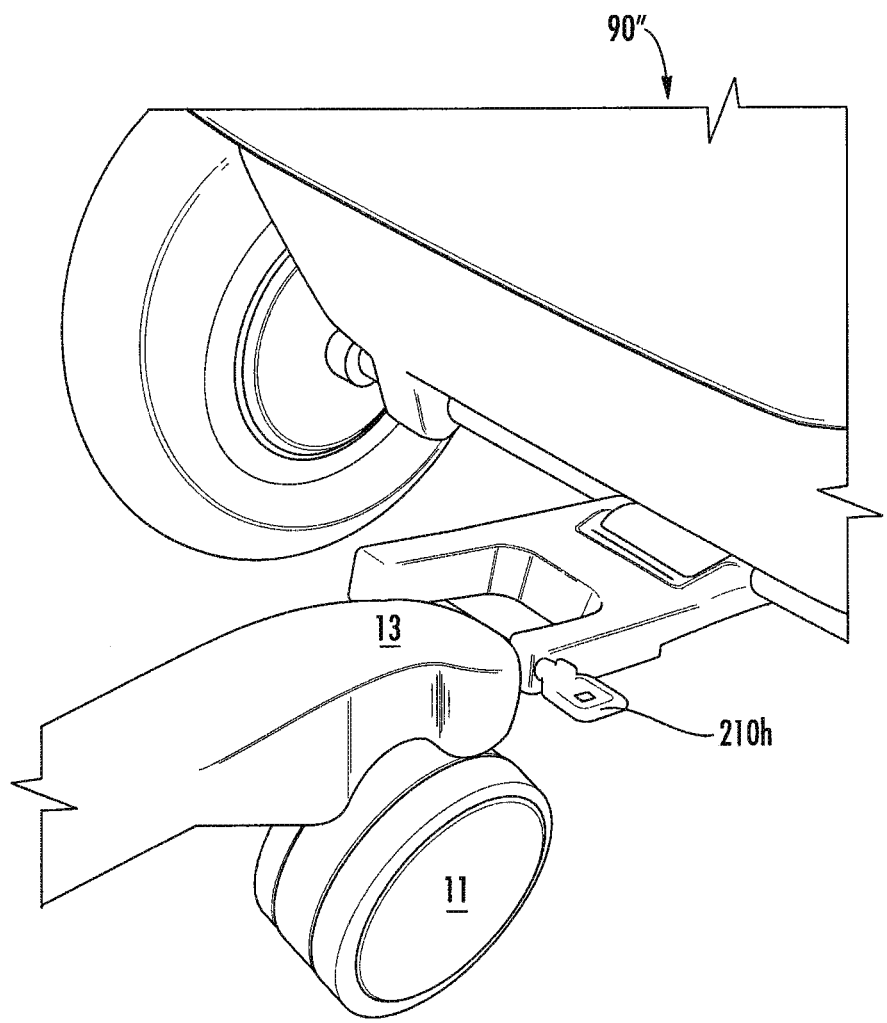
Figure 15D:
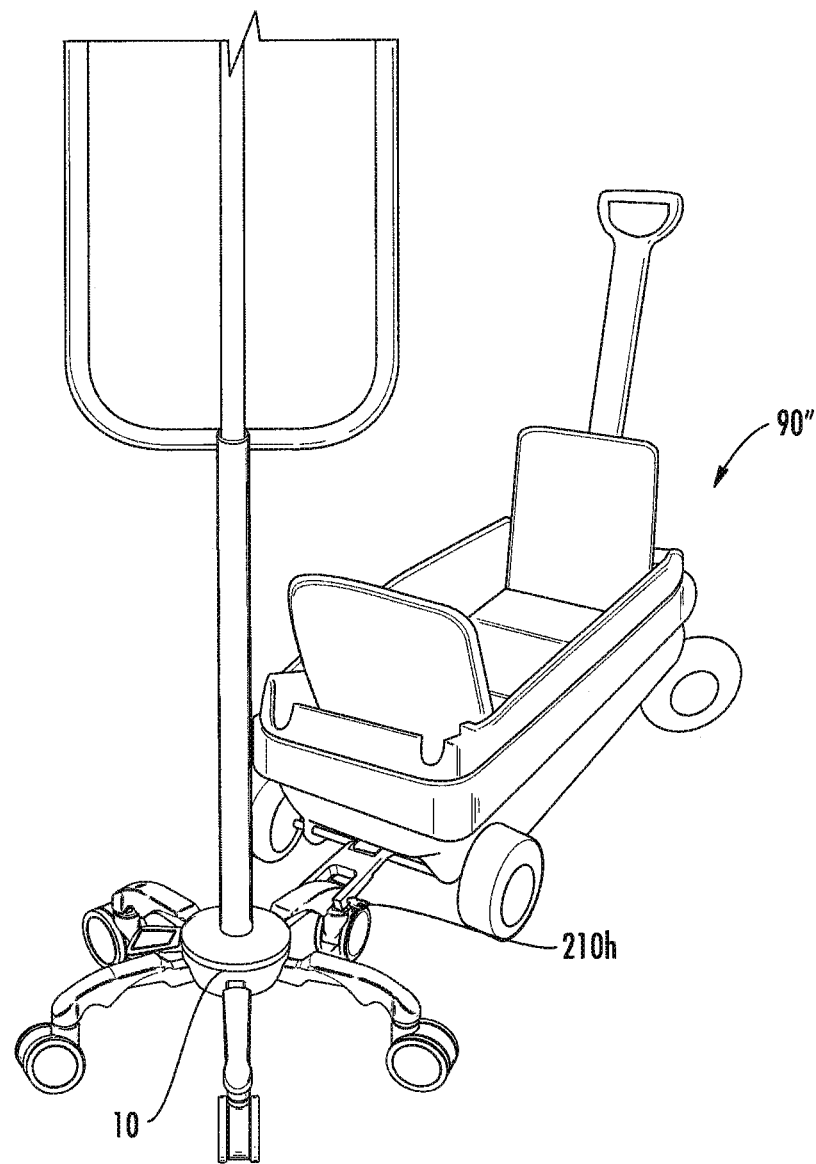
Figure 15E:
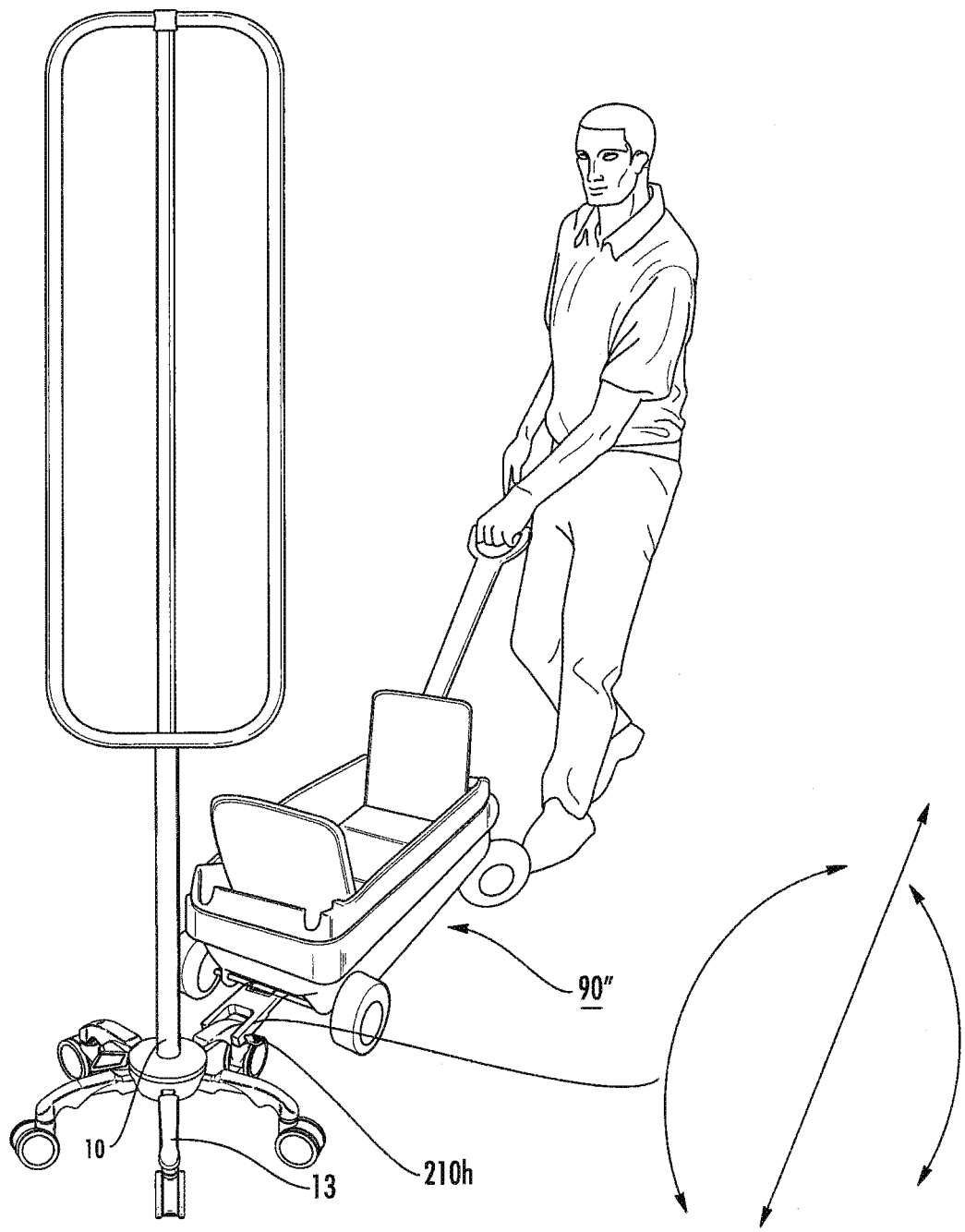
Figure 15G:
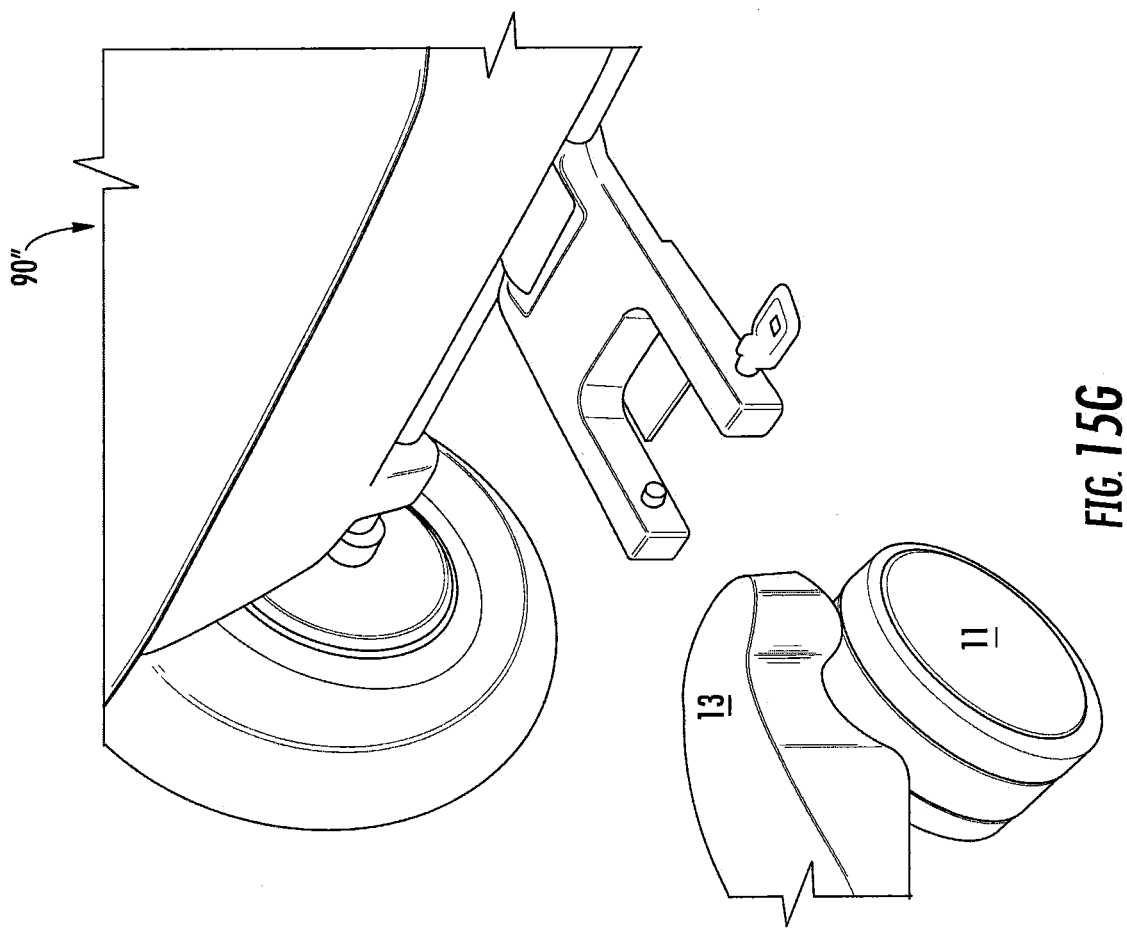

The pole/wagon interface $210h_1$ of the hitch 210h can have a second member 1211 residing below the first member 1210 that includes a flat tongue 1212. The flat tongue 1212 can be stationary and be attached to a lower front end of the mounting block 1215. The tongue 1212 can reside under the arms 1210a of the pivoting upper member 1210 under the gap space 1210g extending between the arms 1210a that can receive the forward upper end of the leg 13 therein. The tongue 1212 may occupy a sub-area of the gap-space 1210g or may extend under one or both arms 1210a, or extend a distance laterally outside of the arms 1210a. A lower surface of a forward edge of one end of the leg 13s of the pole 10 can sit on the flat tongue 1212 and the pivoting member 1210 can pivot down to place the laterally extending attachment members (e.g., typically pins or screws) behind a recessed region of the leg 13r to hold the pole 10 to the wagon 90" while allowing for ease of movement of the wagon and the pole 10. As shown in FIG. 15E by the associated arrows, the wagon 90" can be pulled and the pole 10 can follow the movement of the wagon, e.g., in concert with the wagon and closely spaced apart from the wagon, including side-to-side, longitudinally and rotationally, forward and backward in concert with the wagon.

Referring to FIG. 13B and FIGS. 14A-14D, the wagon/hitch interface $201h_2$ can include a wagon attachment member 1215, which may be provided as a mounting block, optionally rectangular in shape, with a laterally extending channel 1216 that receives an axle 192 of the wagon 90". The wagon attachment member 1215 may also include at least one downwardly extending channel 1218 for receiving a bolt, screw or other attachment member for securing the hitch member 1215 to an underside of the wagon, typically under the cavity 90c and/or closer to the end of the wagon 90" away from the handle 90h.

The first member 1210 and wagon attachment member 1215 can each include laterally extending aligned channels 1230 that hold rods or pins 1231 for the pivoting attachment of the two members 1210, 1215 of the pivot joint J.

As shown in FIGS. 14A-14D, the hitch 210h can include a spring 1220 that is in communication with an inwardly facing end portion of the pivoting member 1210 and an outwardly facing end portion of the wagon attachment member 1215. Thus, the pivoting member 1210 can have a spring-loaded configuration so that a user can manually depress one (longitudinally extending side) arm 1210a of the pivoting member 1210 (typically via foot action) to cause the pivoting member 1210 to raise up and release the leg 13 of the pole 10 (FIG. 15F).

Figure 14A:
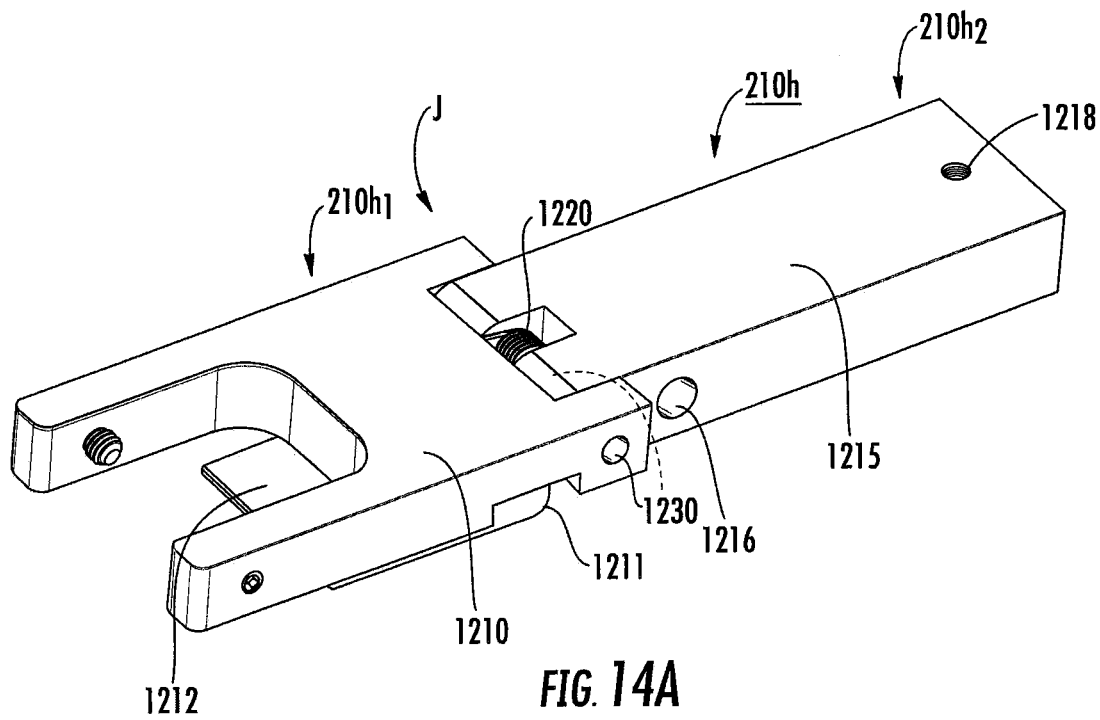
FIG. 14A is an enlarged side perspective view of an exemplary hitch according to embodiments of the present invention.
Figure 14B:
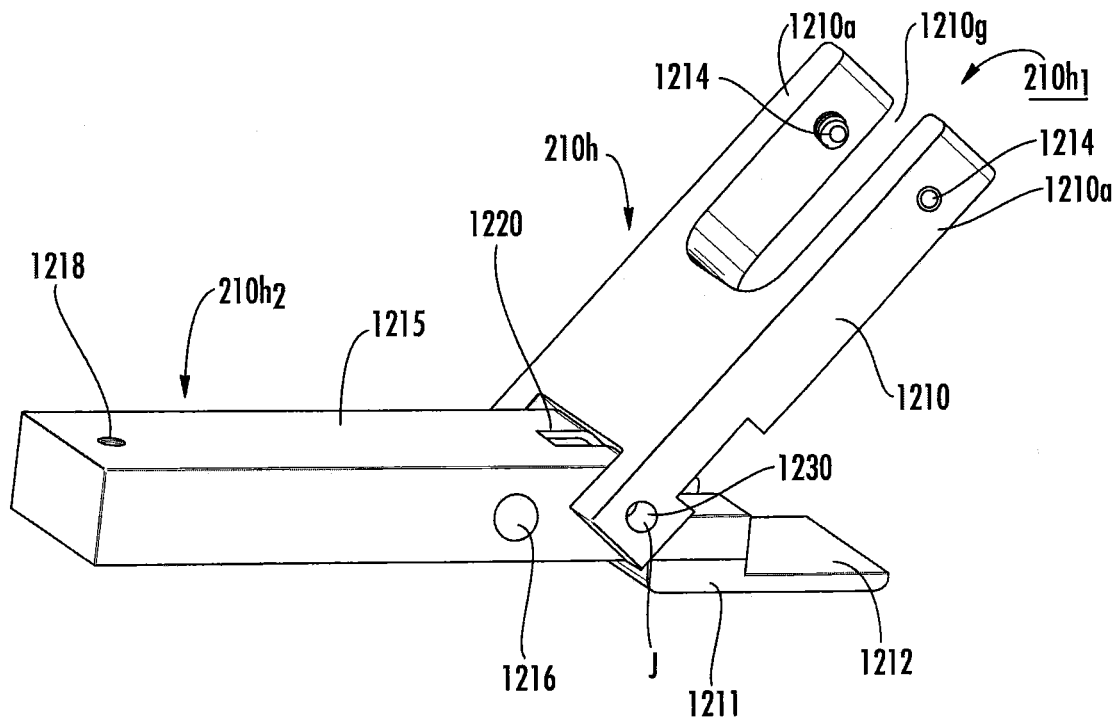
FIG. 14B is an enlarged side perspective view of the hitch shown in FIG. 14A illustrating the hitch in an open or "pivot-up" configuration according to embodiments of the present invention.
Figure 14C:
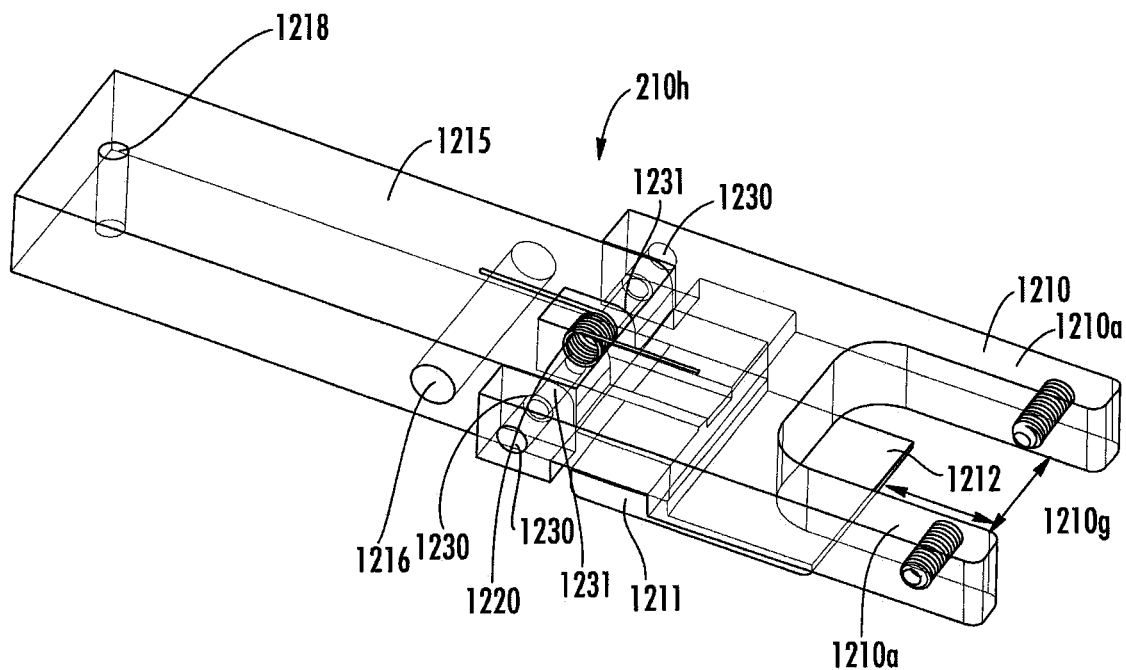
FIG. 14C is a partially transparent side perspective view of the hitch shown in FIG. 14A according to embodiments of the present invention.
Figure 14D:
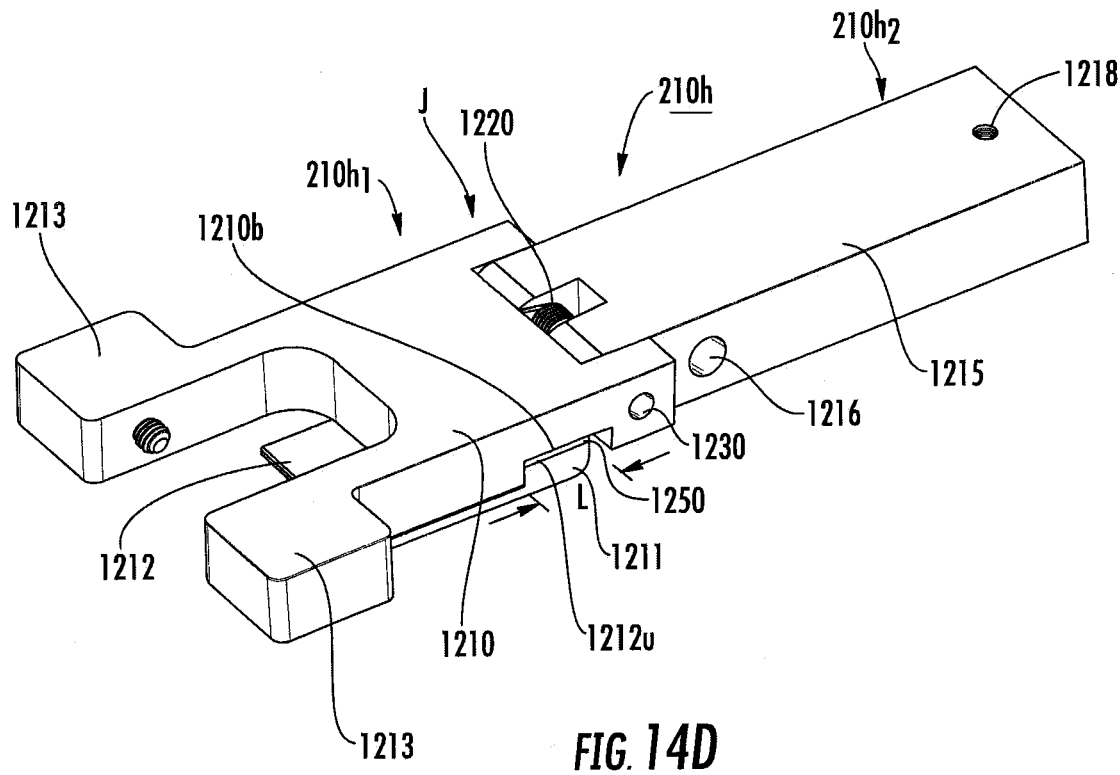
FIG. 14D is an enlarged side perspective view of the hitch, similar to the embodiment shown in FIG. 14A, but with a pad cooperating with the latch and optional laterally extending tabs according to embodiments of the present invention.
Figure 15F:
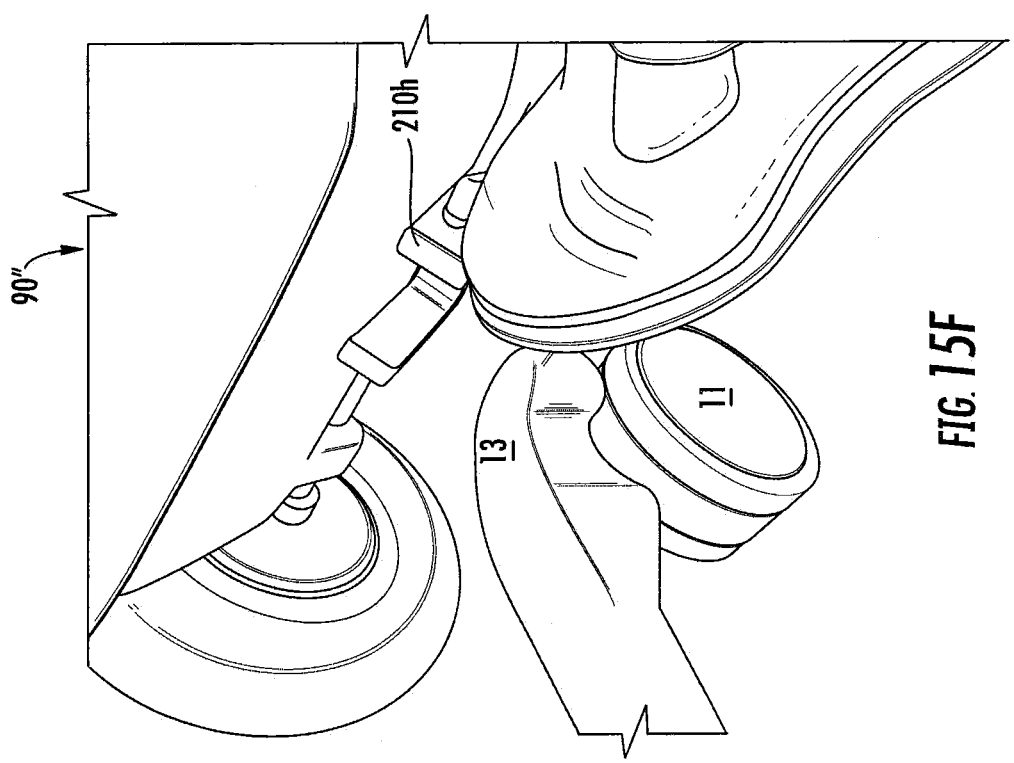
Figure 15H:
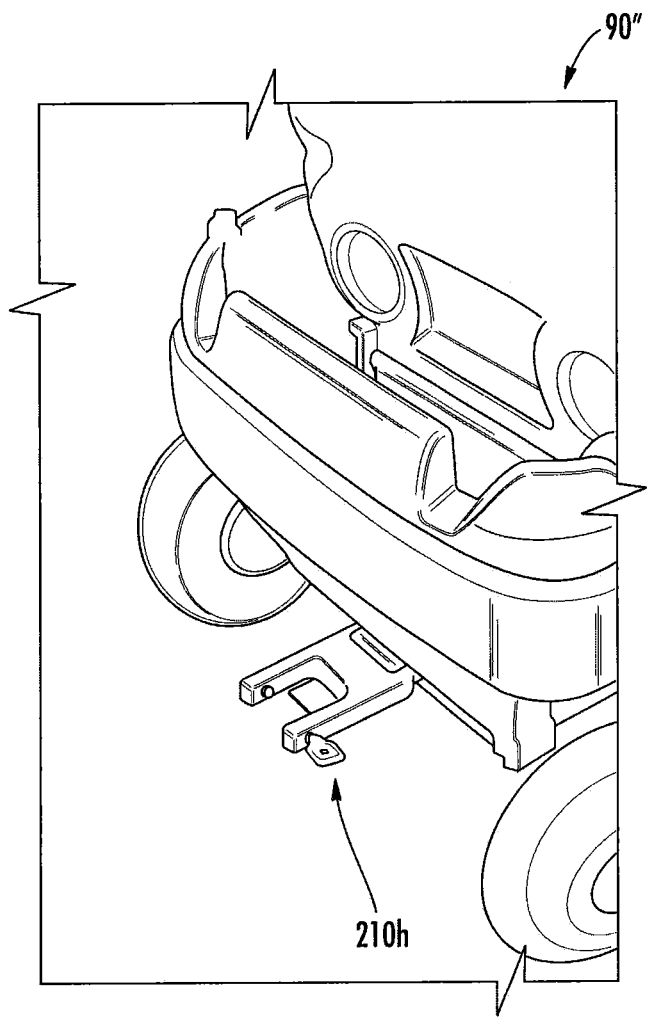

Referring to FIG. 14D, the hitch 210h can have at least one (if a plurality, they can be stacked) planar pad 1250 that is between the upper surface 1212u of the tongue 1212 and the lower surface 1210b of the front block 1210 adjacent the pivot joint J, in front of the mounting block 1215. The pad 1250 can be metal and can communicate with the spring 1220 or pivot joint J between the pivoting (accessory coupling) front member 1210 and the wagon attachment member 1215 to provide a downward force to aid keeping the front member 1210 (e.g., latch or front U-shaped member) engaged with an IV stand on the tongue 1212. The pad 1250 can comprise a spring material and/or configuration so that the pad acts similar to a leaf spring. The pad 1250 can cooperate with the tongue 1212 to keep the IV stand and latch 1210 from separating. The pad 1250 can have a relatively short length relative to the length of the tongue 1212 and/or overlying front member 1210, typically less than 50% the length of either of those two components, such as, for example, between about 1 inch to about 3 inches long. The pad 1250 can extend across the entire width, or at least 75% thereof, of the tongue 1212 and/or front block 1210.

The pad 1250 can be relatively thin, such as having a thickness of between about 0.10 inches to about 0.25 inches. The pad 1250 may comprise a metal alloy, typically an aluminum alloy. The pad material can comprise 6061-T6 aluminum. In some embodiments, the pad 1250 can have a thickness between about 0.125 inches and 0.25 inches, typically between about 0.150 inches and 0.175 inches. Where more than one pad 1250 is used (e.g., stacked) the cumulative thickness can be between 0.125 inches and 0.25 inches, typically between about 0.150 inches and 0.175 inches.

The hitch 210h may also include at least one laterally extending (foot or hand) lift tab 1213 for the external wagon/accessory attachment interface $210h_1$ for facilitating disengagement from the IV pole/other accessory. As shown, the at least one lift tab 1213 can include right and left side tabs 1213 that extend outward a distance from the sides of the front member 1210, typically a distance of between about 0.25 inches and 2 inches, more typically between about 0.5 inches and 1.5 inches, relative to a segment of the front member 1210 rearward thereof The tabs 1213 can extend forward to the end of the front block on opposing sides of the center space or may terminate to a more narrow leading end (not shown) at the outermost segment of the front member 1210.

Figure 7:
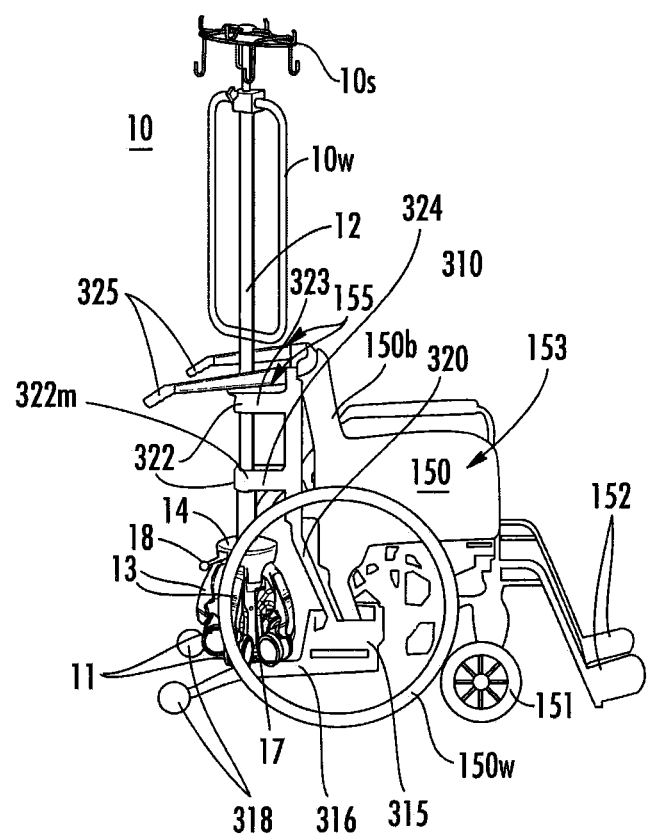
FIG. 7 is a side perspective view of a pole in a retracted (wheel lifted) configuration while docked to a wheelchair docking mount of a wheelchair according to embodiments of the present invention.

Referring now to FIG. 7, the pole 10 can be configured to engage a docking system 310 attached to a wheel chair 150. Typically, as is conventional, the wheel chair 150 includes large rear wheels 150w, smaller front wheels 151, a back 150b, leg supports 152 and a seat 153. The larger rear wheel 150w is shown without the spindles for ease of discussion. The docking system 310 can include a base 315 that resides between, typically aligned with, the axles of the large wheels 150w. The base 315 can include backwardly extending legs 316 that hold wheels 318. The legs 316 can taper down from the base 315 to the wheels 318. The wheels 318 can extend out a distance of between 1 inch to 12 inches, typically between 2 inches and 10 inches, behind the large wheels 150w of the wheelchair typically within a foot print or space that corresponds to a separation distance of the large wheels 150w. The wheels 11 of the pole 10 can reside between the wheels 318 of the docking system 310 when in a stowed configuration as shown. As described above, the pole 10 can have a different configuration than shown. Where the pole 10 is a transformable pole, it can have a different transformable pole configuration than shown with different numbers of wheels/casters, different size wheels/casters and a different lift and/or wheel-extend lever and mechanism.

The base 315 of wheel chair docking system base 310 can also include an upright support member 320 that holds at least one accessory (e.g., pole) attachment member 322. The at least one attachment member 322 can include first and second mast attachment members 322m that can hold a vertical segment of a mast 12 or pole 10, one above the other, that face away from the seat 153. When docked to the docking system 310, the legs/wheels of the pole 10 can be raised as shown.

The upright support member 320 can have a telescopic and/or slidably adjustable configuration to allow for the pole attachment member 322 (e.g., lower and upper members 323, 324), to be positioned at different height locations. The upright member 320 may have a curvilinear configuration to angle back as it rises above the base before extending straight up for a distance.

In some embodiments, the pole docking system 310 can include handle attachment members 325 that can be attached to handles 155 of the wheelchair 150. The handle attachment members 325 can be attached to the upright member 320 of the docking system 310.

FIGS. 16A-16H illustrate another embodiment of a wheelchair docking system 310'. The docking system 310' can include a base 315' attached to the wheelchair 150 between the large wheels 150w that supports an upwardly extending support member 320'. The docking system 310' can also include at least one accessory attachment member 322' that can releasably engage a pole 10 or other accessory.

In some embodiments, the at least one attachment member 322' can include at least one outwardly extending attachment member 1322 which can be provided with first and second spaced apart outwardly extending right and left side arms 1322a. The arms 1322a may be configured to pivot up and down, typically in concert, to engage and release a horizontally extending and/or lateral segment 10h of an accessory pole 10, for example.

The at least one accessory attachment member 322' can also optionally include an outwardly extending mast attachment member 322*m* that releasably (i.e., detachably) hold a vertical segment of the accessory, e.g., mast 12 or other segment of the pole 10.

The arms 1322*a* can have a curved upward facing surface. The curved surface can have a radius of curvature corresponding to the lateral tube segment 10*h* of the pole 10. The curved surface of the arms 1322*a* can extend outward from the back of the chair and reside laterally closer to or further spaced apart from the wheelchair 150 than the upper longitudinally extending mast attachment member 322*m*, shown as closer in FIG. 16A, for example. The centerlines of the curved surface s of the arms 1322*a* and the mast attachment member 322*m* can be offset by about 1-5 inches, more typically about 1-2 inches, in some embodiments.

In some embodiments, the docking system 310' can include angled, laterally extending struts 360 that extend inward from the upwardly extending support member 320' with ends 362 that can attach to the wheelchair 150, typically to tubular structures 150*t* (FIG. 17C) of the wheelchair frame. FIG. 18 illustrates that the struts 360 are not required.

Figure 17A:
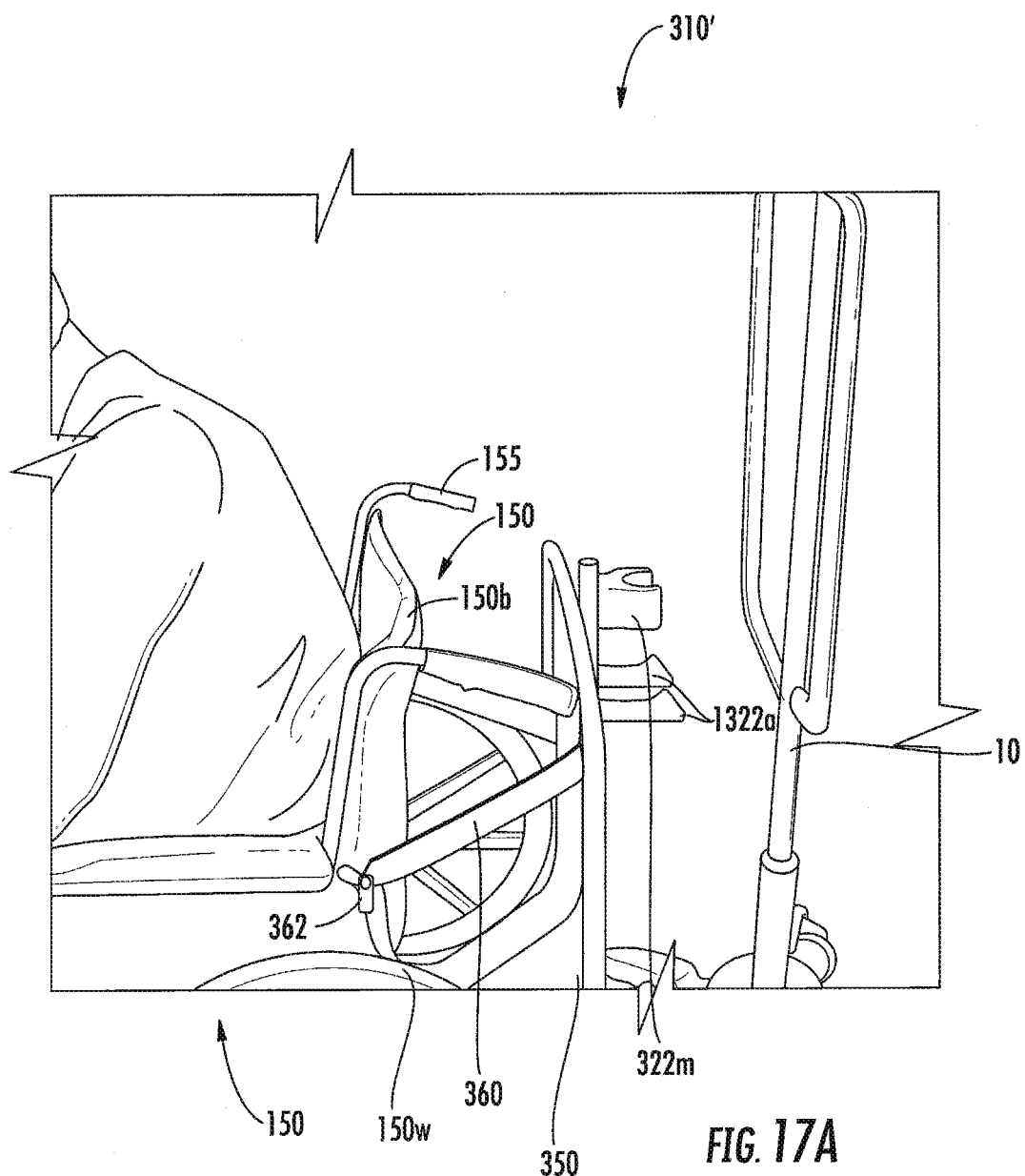
FIGS. 17A-17E are an exemplary sequence of docking/using and releasing the pole/wheelchair shown in FIGS. 16A-16H according to embodiments of the present invention.
Figure 17B:
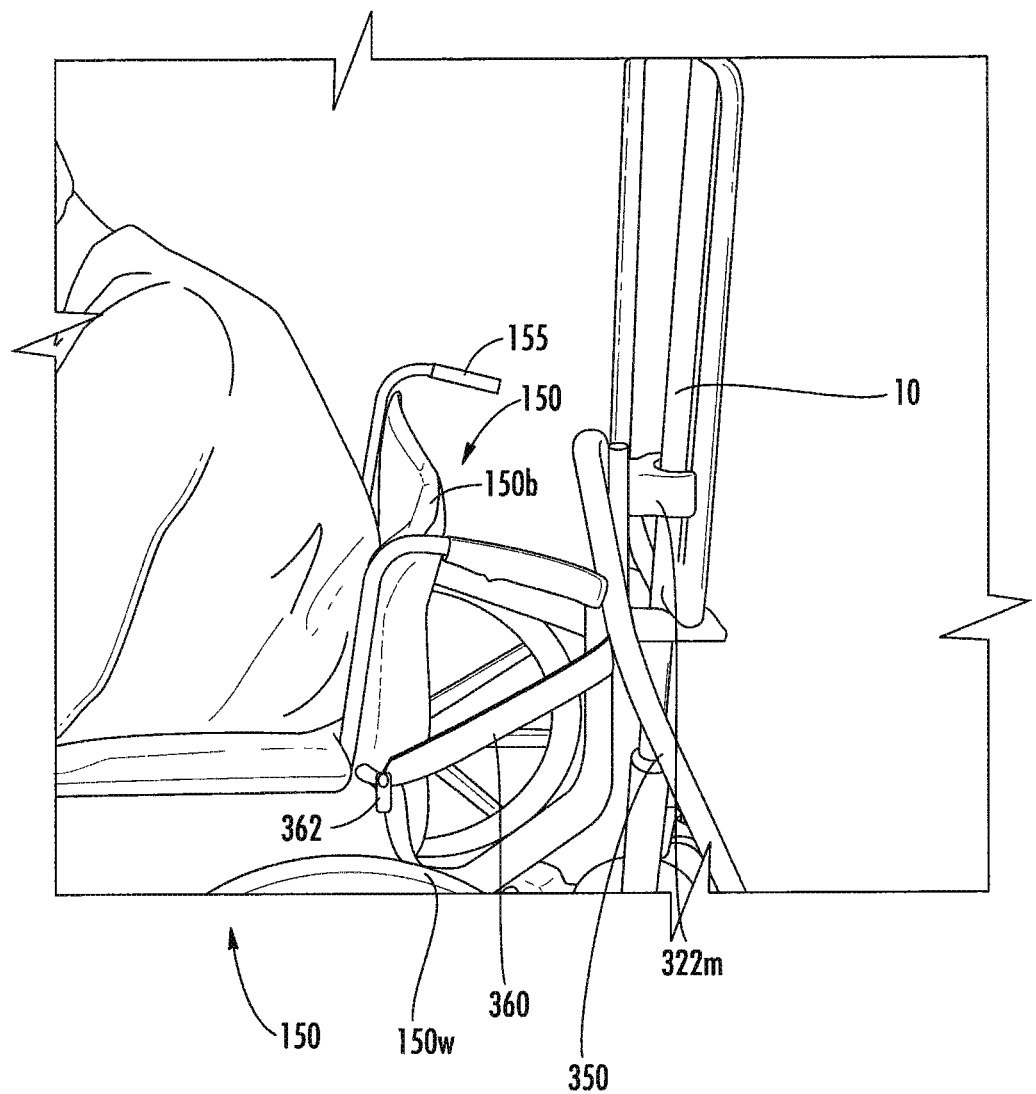
Figure 17C:
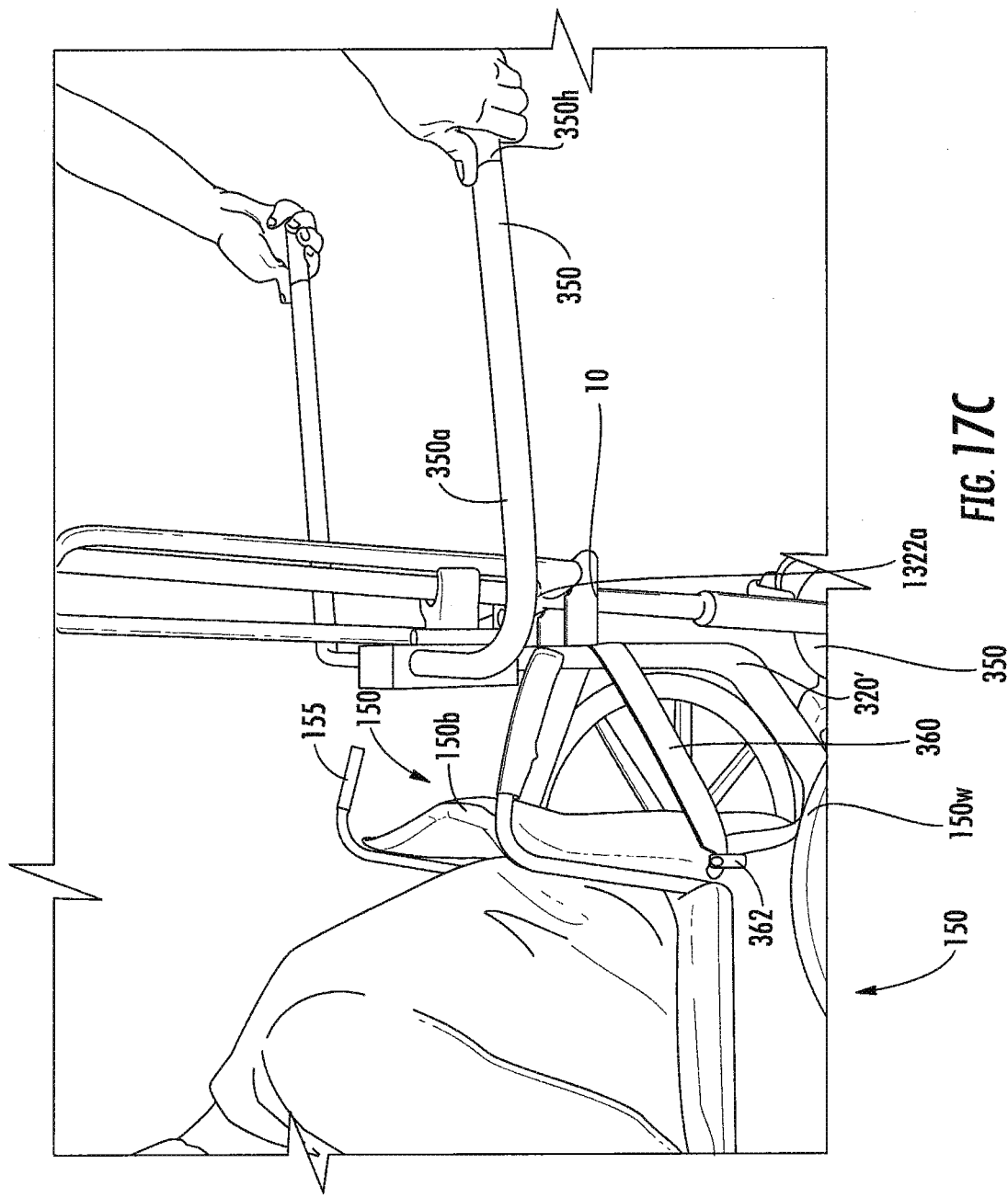
Figure 17D:
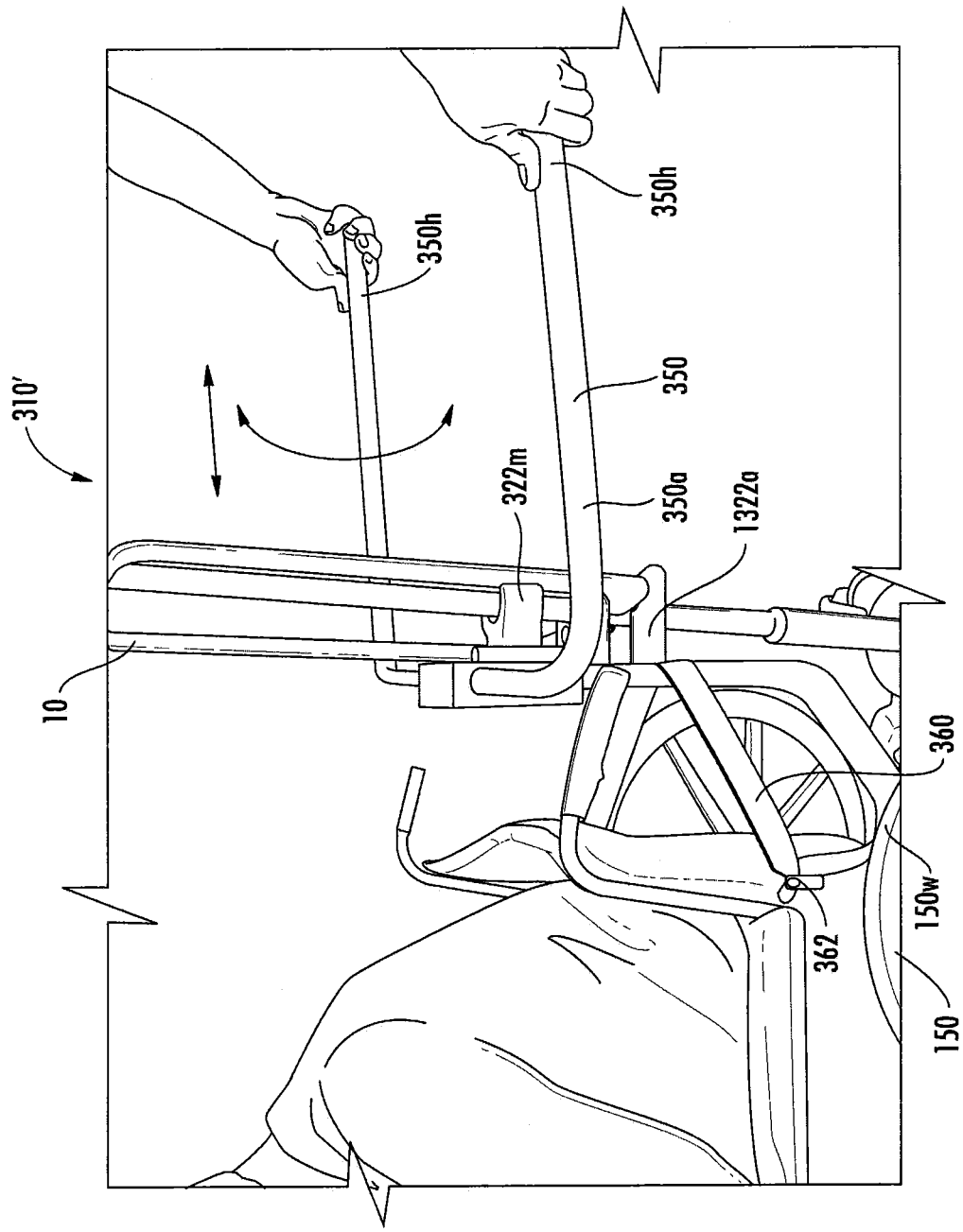
Figure 17E:
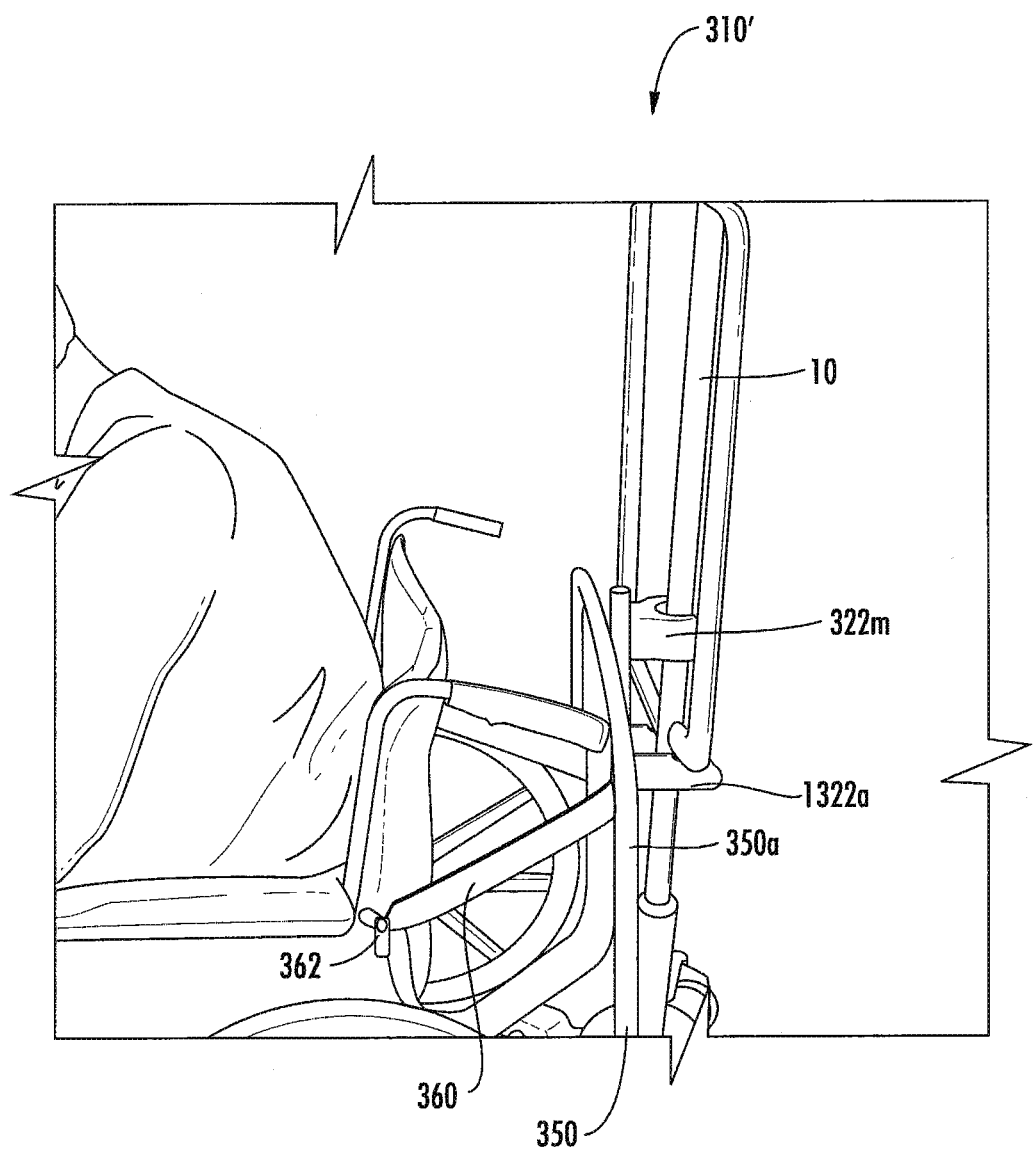
Figure 18:
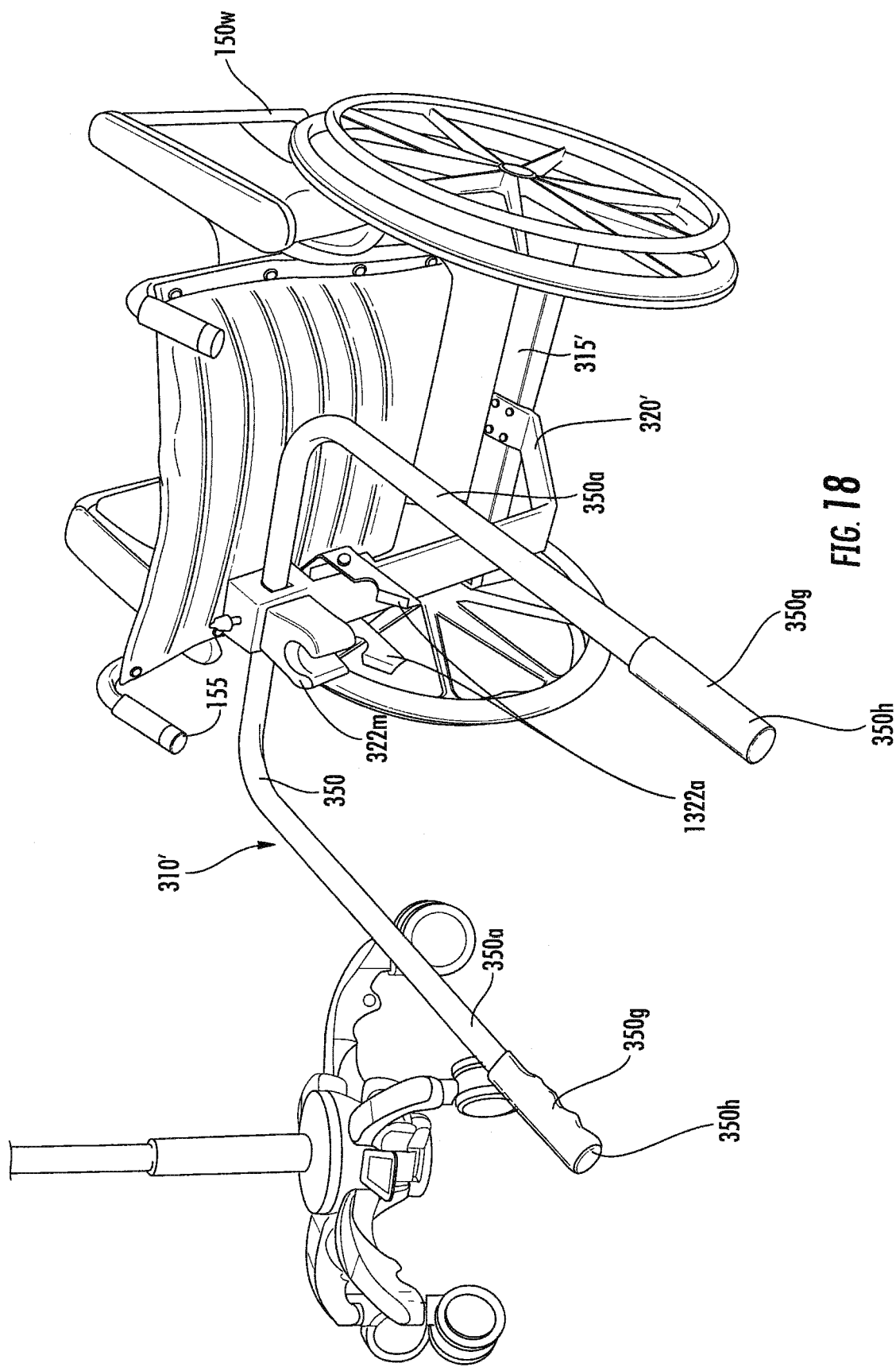
FIG. 18 is a rear perspective view of another embodiment of the wheelchair docking interface/system according to embodiments of the present invention.

The docking system 310' can, in some embodiments, also include a pivoting handle member 350 that can provide a pair of arms 350 as supplemental handles 350*h* for pushing the wheelchair 150 (FIGS. 17C, 17D, 18, for example). The supplemental handles 350*h* may include elastomeric hand grips 350*g* (FIG. 18) on an end portion thereof. The hand grips 350*g*, where used, may be provided as a sleeve or overmolded member/feature, for example.

The pivoting handle member 350 can have a first retracted configuration (FIG. 17A) to reside with the handle arms 350*a* in a vertical or substantially vertical orientation (e.g., less than 20 degrees from vertical) adjacent a rear of the wheelchair, inside the space of the large wheels 150*w*. While shown in a (preferred) downwardly extending orientation for the retracted position, the arms 350*a* may reside in an upwardly extending orientation in the retracted position (not shown).

In the extended position (FIGS. 16F, 17C, 18), the handle member 350 can be configured so that the handle arms 350*a* reside rear of the seat 150*b* and/or onboard handles 155 and have a length L sufficient to extend a distance rearward of an accessory/e.g., pole when the accessory is attached to the docking system 310'. The length L may be, for example, between about 6 inches to 48 inches, typically between about 12 inches to about 36 inches, and more typically between about 18 inches and about 24 inches such as about 20 inches (FIGS. 16B, 16H, 17C). The arms 1322*a* can extend horizontally or substantially horizontally (e.g., less than 20 degrees from horizontal) in the "use" configuration.

Figure 16A:
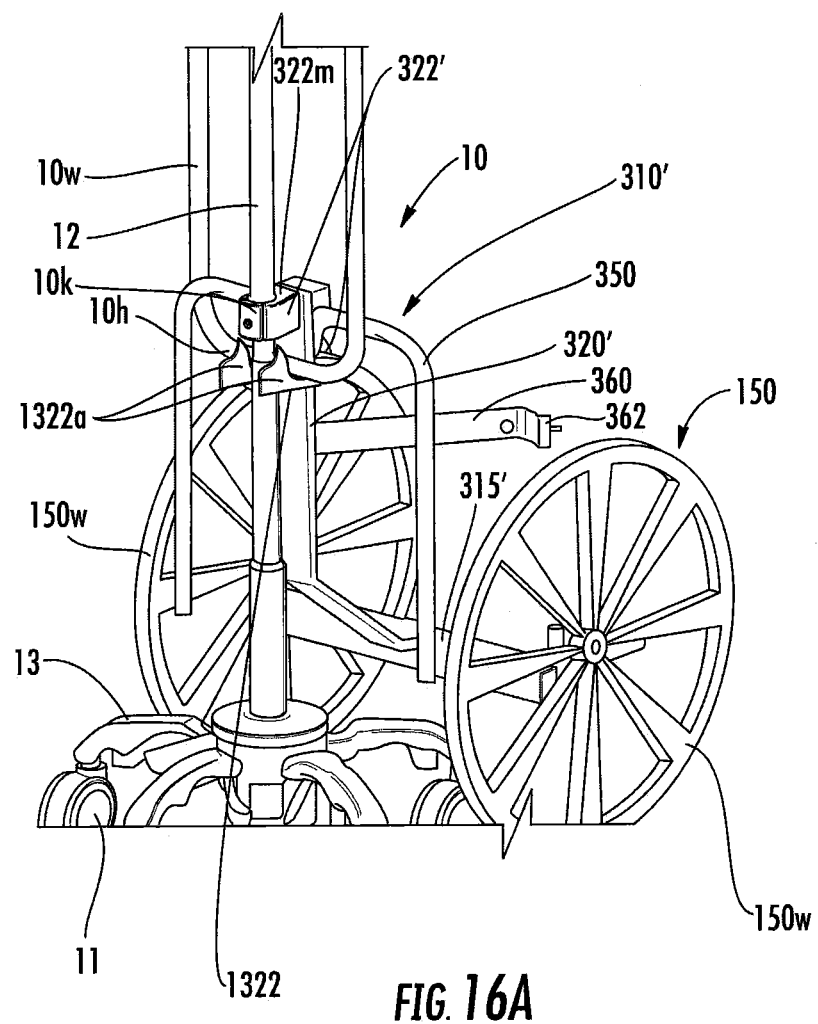
FIG. 16A is a rear, side perspective view of a wheelchair interface/docking system with a releasable pole according to embodiments of the present invention.
Figure 16B:
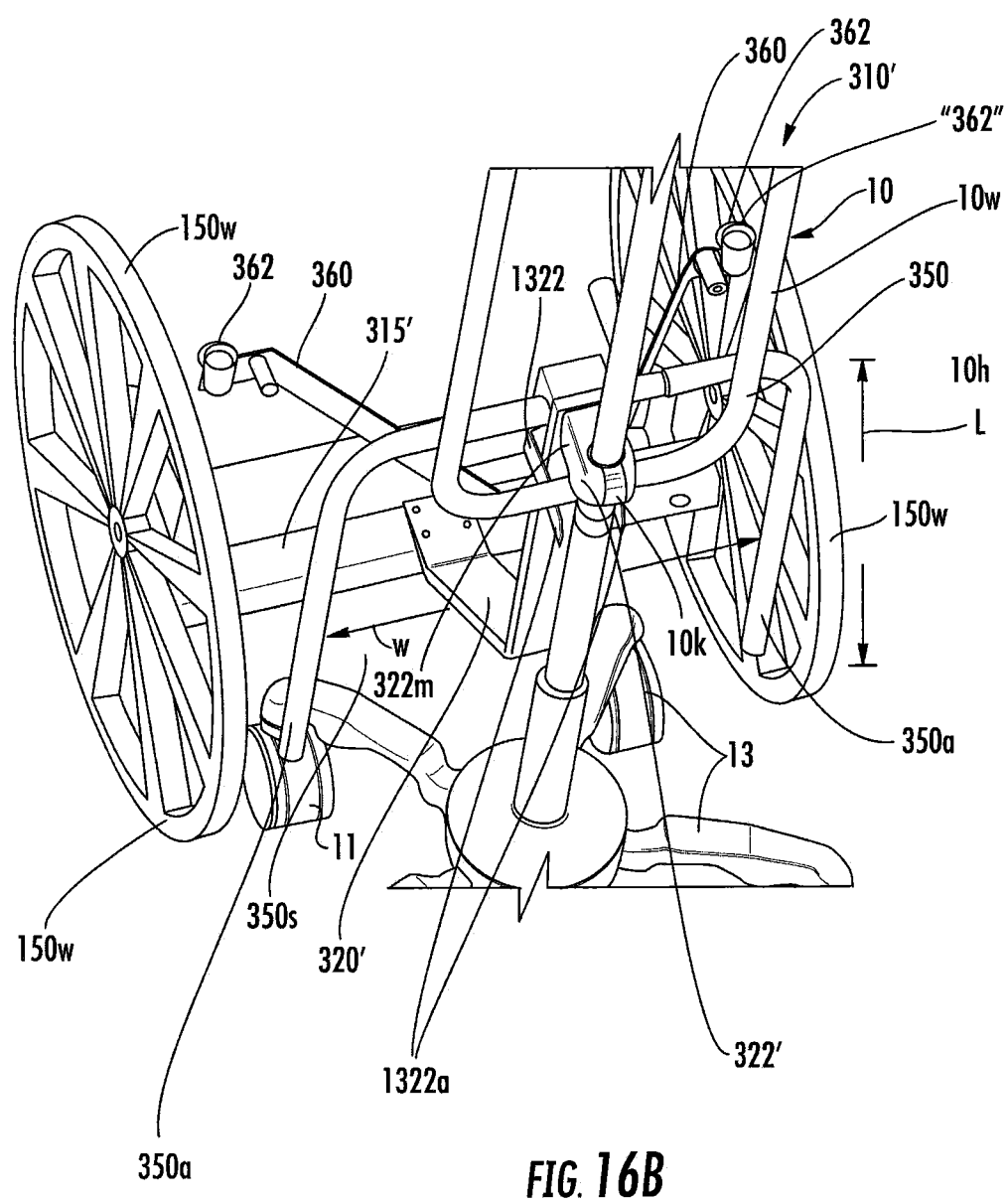
FIG. 16B is a rear, top perspective view of the interface and pole shown in FIG. 16A.
Figure 16C:
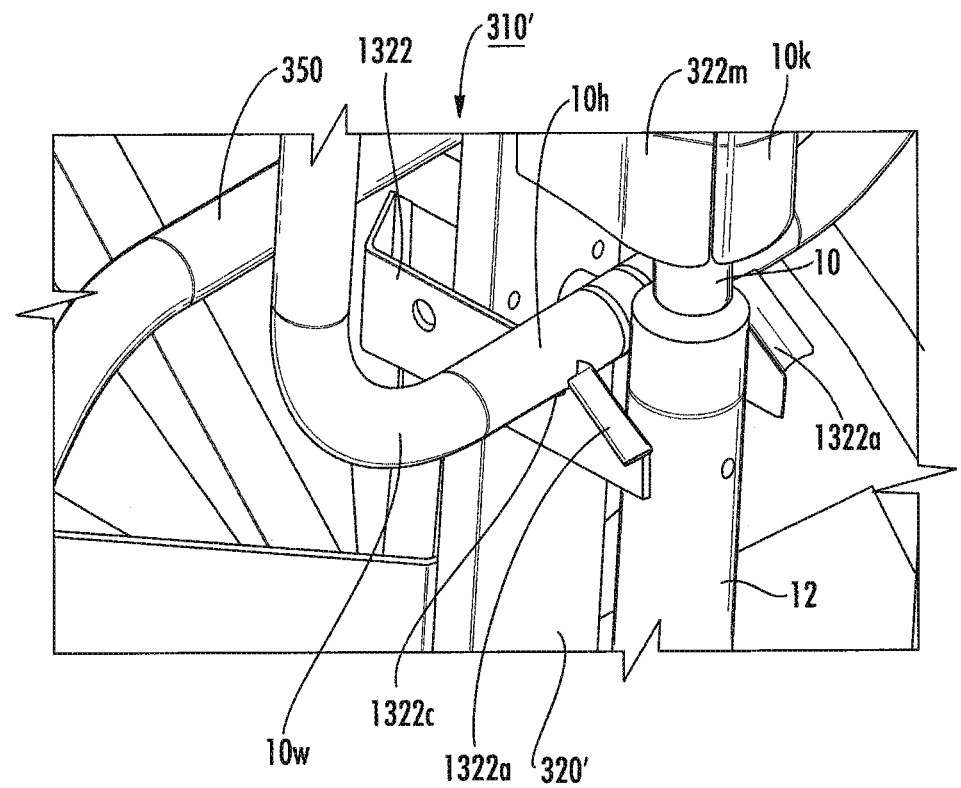
FIG. 16C is an enlarged side perspective view of a portion of the wheelchair docking system shown in FIG. 16A.
Figure 16D:
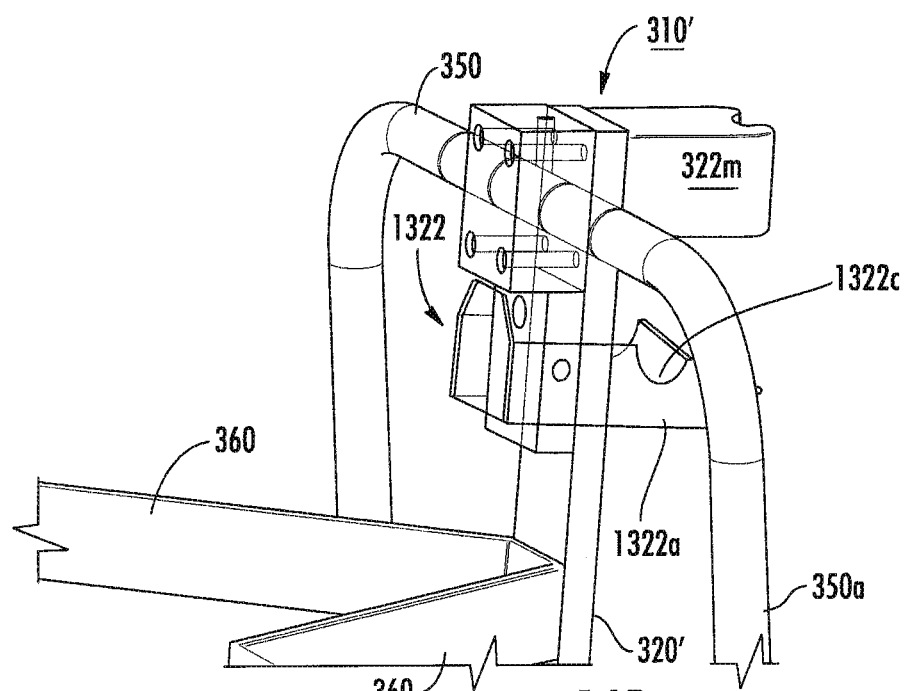
FIG. 16D is a front, side perspective view of a portion of the wheelchair docking system shown in FIG. 16A with certain components shown in transparent view.
Figure 16E:
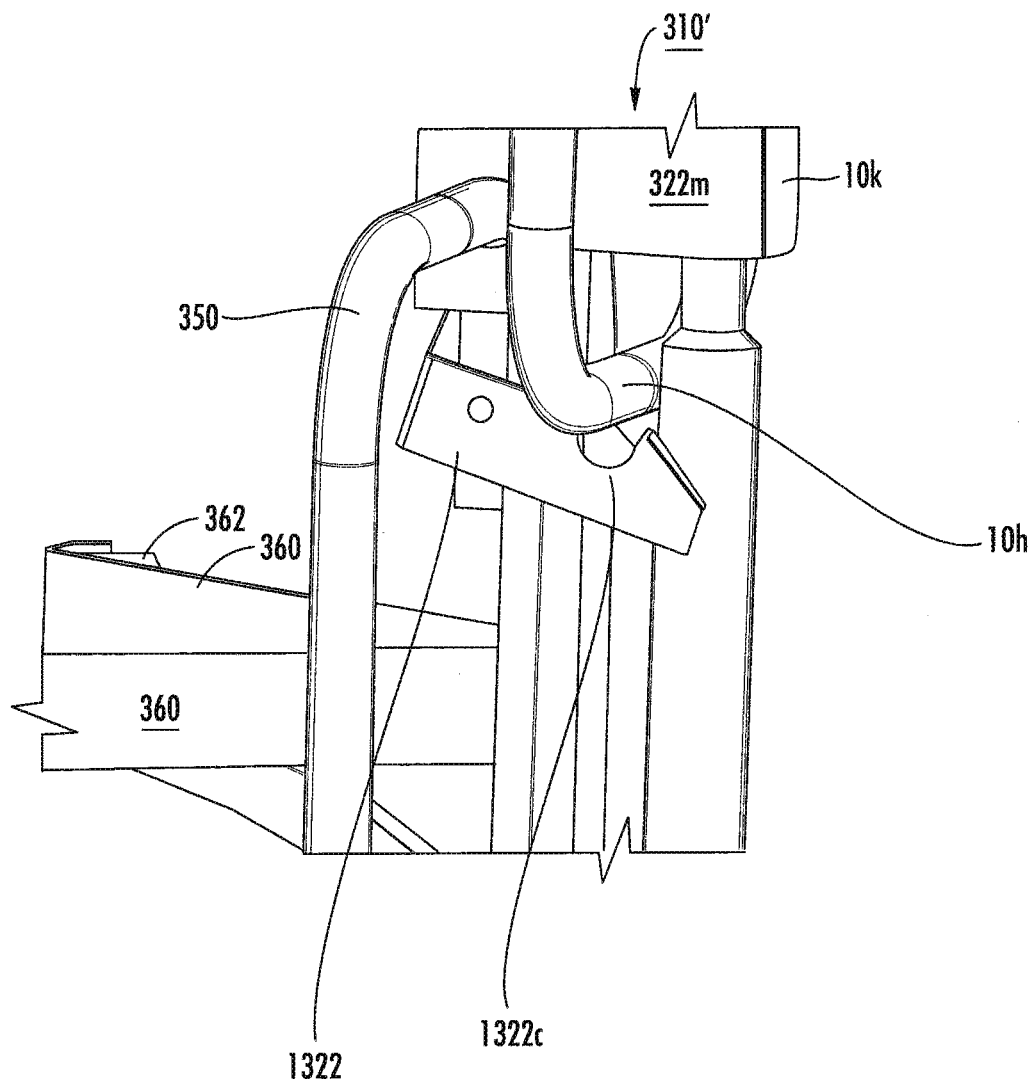
FIG. 16E is a side perspective view of a portion of the wheel chair docking system shown in FIG. 16C, illustrating a pivoting position of an arm of the docking system according to embodiments of the present invention.
Figure 16F:
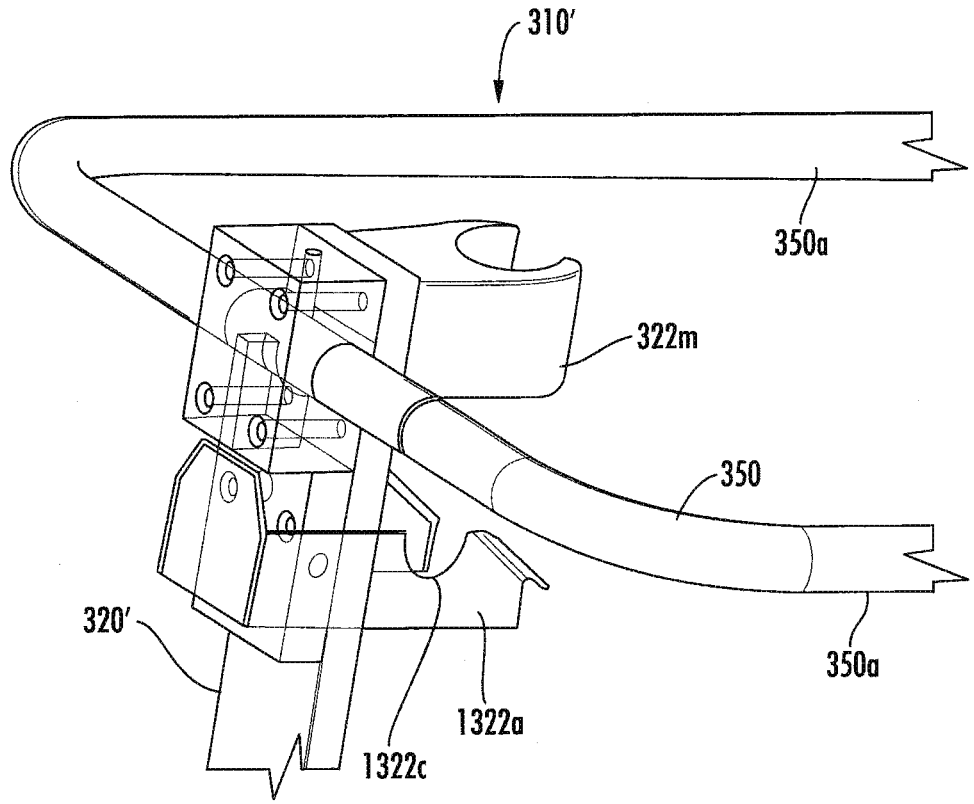
FIG. 16F is an enlarged side perspective view of the wheelchair docking system shown in FIG. 16A illustrating push arms pivoted outward relative to the position shown in FIG. 16A and the pole disengaged from the wheelchair docking system according to embodiments of the present invention.
Figure 16G:
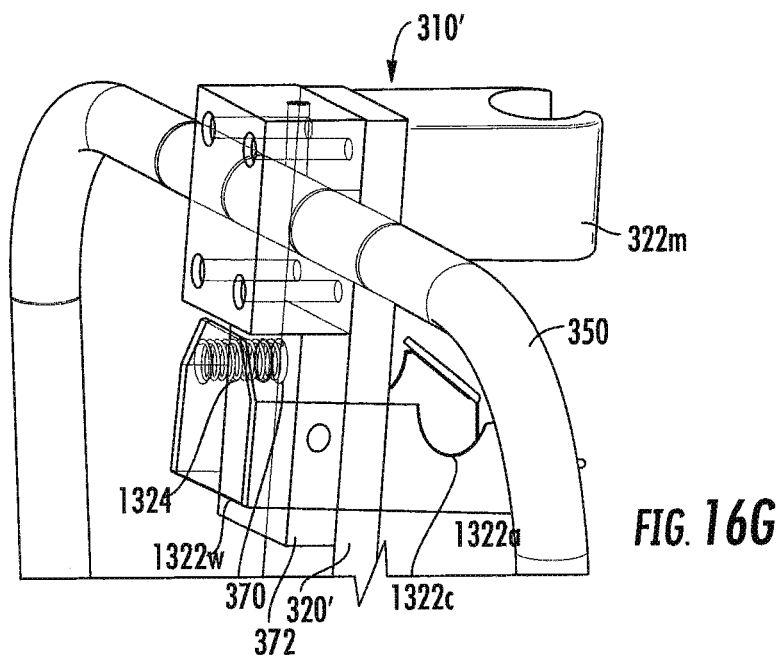
FIG. 16G is an enlarged side perspective view of the wheelchair docking system shown in FIG. 16A illustrating push arms pivoted downward and the holding bracket disengaged from the pole.
Figure 16H:
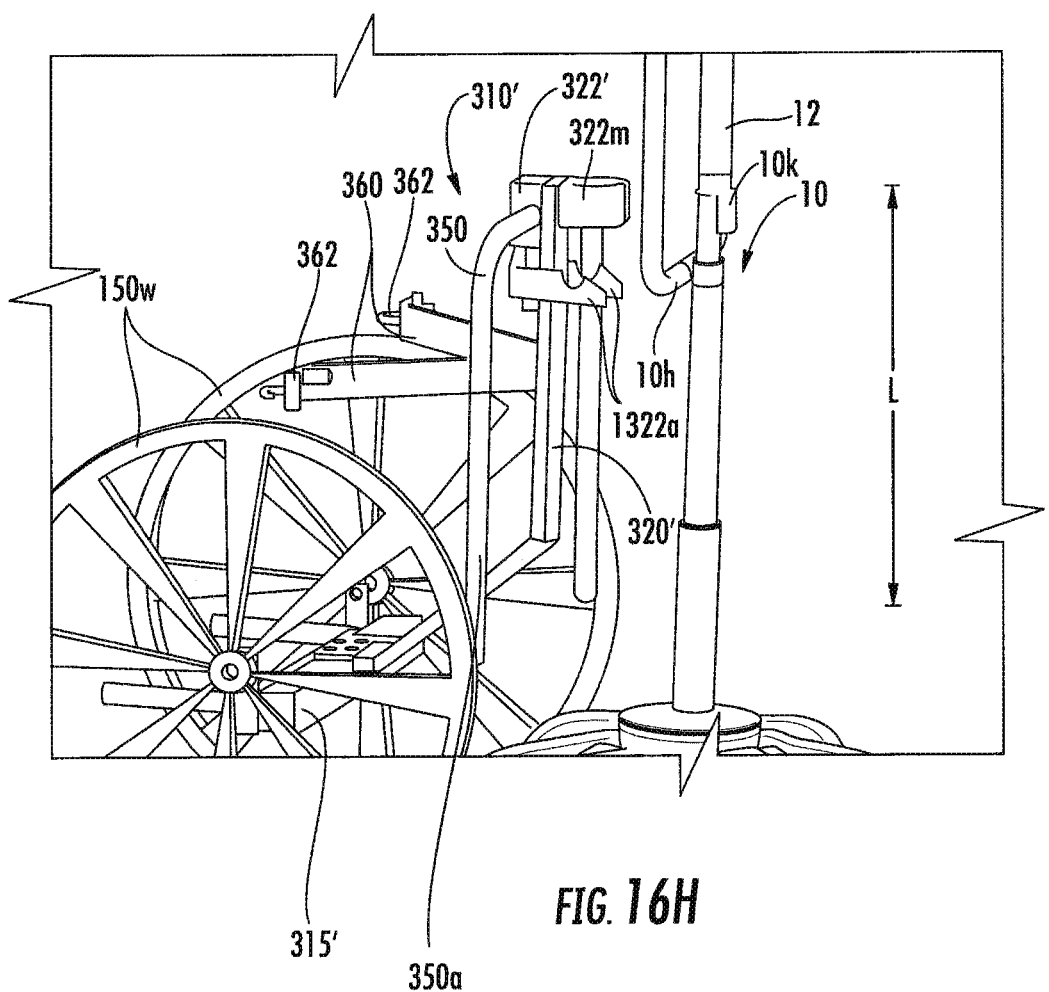
FIG. 16H is a side perspective view of the wheelchair docking system disengaged from the pole and the push arms down according to embodiments of the present invention.

The pivoting handle member 350 can be a "U" shaped member 350 that can pivot up and down between the home/storage configuration and the outwardly extending configuration, see FIG. 16A and FIG. 16F, for example.

As shown in FIG. 16H, for example, the pivoting handle member 350 can reside above the attachment member 1322 that releasably engages a horizontally extending segment 10*h* of an accessory and below the mast attachment member 322, where used. The pivoting handle member 350 can have a gap space 350*s* (FIG. 16B) with a width "W" that is sufficient to allow the accessory to reside between the arms 350*a*. The width W can be, for example, in a range of about 18 inches to about 48 inches, more typically between about 18 inches and 32 inches, so as to be no wider than the maximal width of the wheelchair itself and may be configured so that when stored, the arms 350*a* are inside a boundary of and adjacent the respective wheelchair wheels 150*w*.

Referring to FIGS. 16C, 16D and 16E, for example, the pivoting attachment member 1322 can detachable engage the horizontal segment(s) of an accessory in curved upper channels 1322*c*. The member 1322 can pivot down (FIG. 16E) to disengage or release the accessory 10*h* and pivot up to trap right and left side horizontal segments of the accessory, typically below the key 10*k* of the mast holding segment 322*m*. FIG. 16F illustrates that the pivoting attachment member 1322 can be attached to the upwardly extending support via a pivoting joint with a spring 1324 for a spring-loaded attachment configuration to provide a secure, snug attachment to the accessory. The spring 1324 can be trapped between a back wall 1322*w* of the pivoting attachment member and a channel 372 in a block 370 attached to the upwardly extending member 320'. However, other attachment configurations may be used.

As shown, for example in FIG. 17D by the appended arrows, a user can readily push and pull the wheelchair 150 with the accessory pushed and pulled in concert so as to follow the movement of the wheelchair 150, e.g., in concert with and closely spaced apart from the wheelchair, including side-to-side, longitudinally and rotationally, forward and backward in concert with the wheelchair using the handles 350*h*.

It is also contemplated that walkers used for patient ambulatory stabilization when moving can include a docking system similar to that described above for the wheelchair, wagon or canister that releasably engages a pole 10 or other accessory (not shown).

Figure 8:
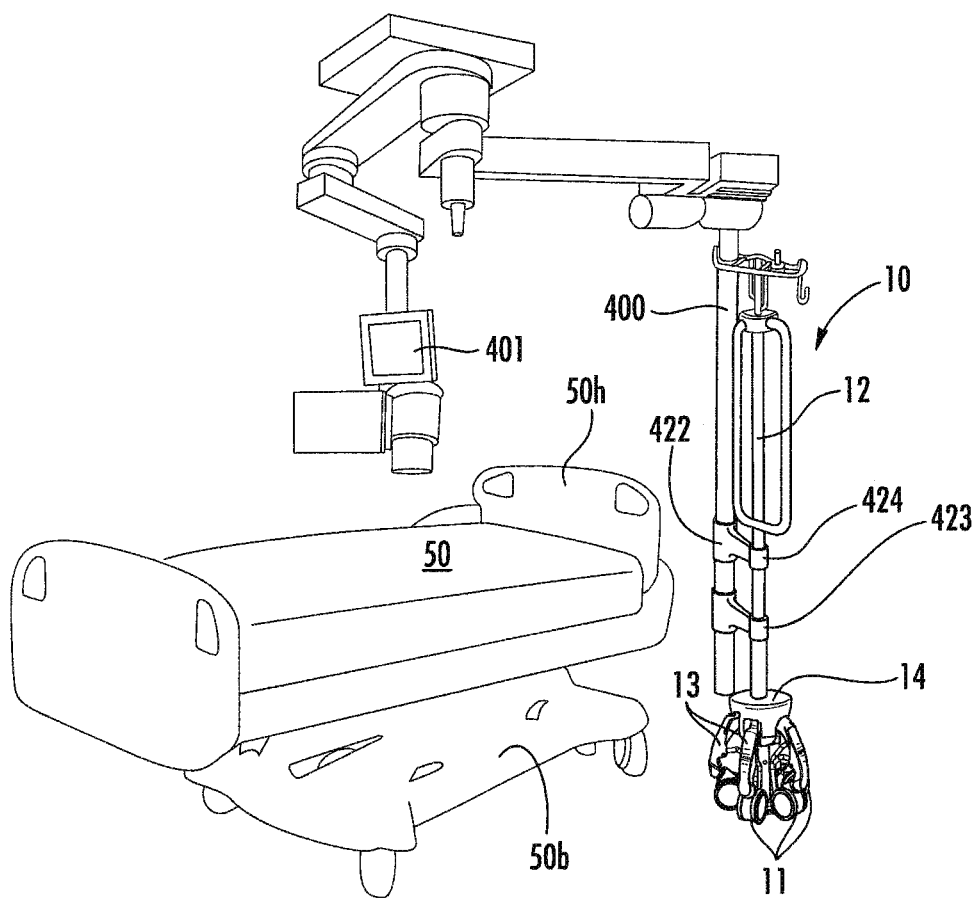
FIG. 8 is a side perspective view of a pole in a retracted configuration, docked to booms and/or column mounts in a hospital or clinic room according to embodiments of the present invention.

FIG. 8 illustrates a pole 10 that can provide dock to a tower or vertical boom 400 of a medical room, such as a hospital room, a surgical room, a diagnostic room with diagnostic equipment such as CT or X-ray equipment 401. The boom or tower 400 can include at least one pole attachment member 422. The pole 10 can include ends of the pole attachment member 422. The attachment member 422 can remain on the tower or boom 400 or move with the pole 10 when disengaged and the wheels 11 supporting the pole. Where more than one pole attachment member is sued, e.g., members 423, 424, one can remain on the tower or boom 400 and another can travel with the pole 10. The pole 10 can have a smaller diameter attachment member relative to the tower or boom 400. The attachments 422 can allow the pole 10 to pivot or rotate relative to the tower or boom 400 and may also optionally telescope or extend to allow for lateral spacing adjustment which may allow for better positioning of certain accessories relative to a patient, e.g., an oxygen tank 20, for example. As described above, the pole 10 can have a different configuration than shown, including a different transformable pole configuration with different numbers of wheels/casters, different size wheels/casters and a different lift and/or wheel-extend lever and mechanism.

In some embodiments, the pole 10 of whatever use or uses including those described hereinabove, can be configured to be safely used in an MRI suite including in a magnetic field of an MRI Scanner. Thus, the pole 10 can be configured with non-ferromagnetic materials and components.

Figure 9A:
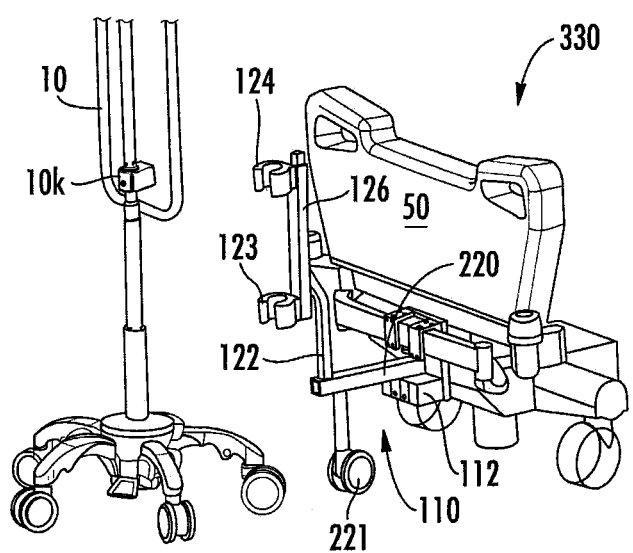
Figure 9B:
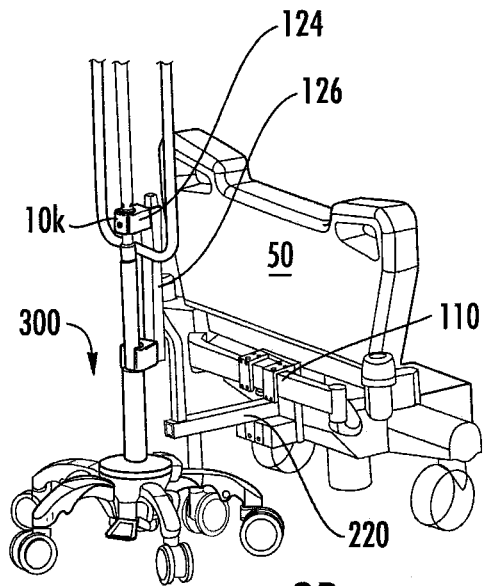
Figure 9C:
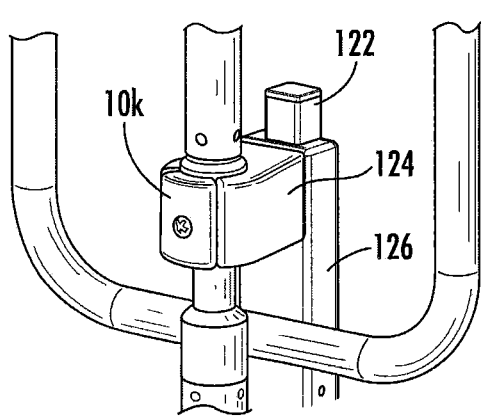
Figure 9D:
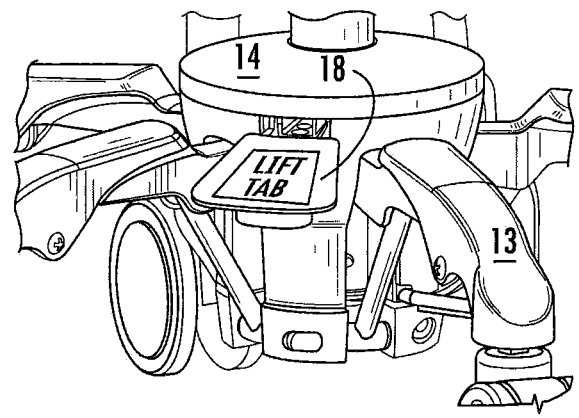
Figure 10A:
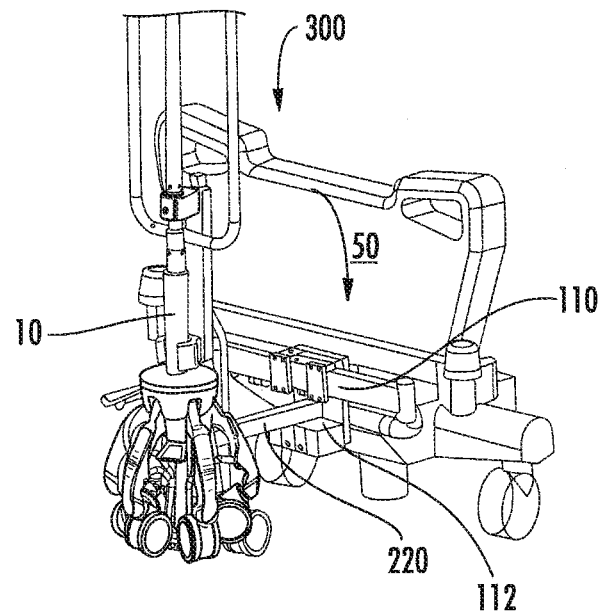
FIGS. 10A-10D are sequential views illustrating exemplary unloading/release steps of the pole according to embodiments of the present invention.
Figure 10B:
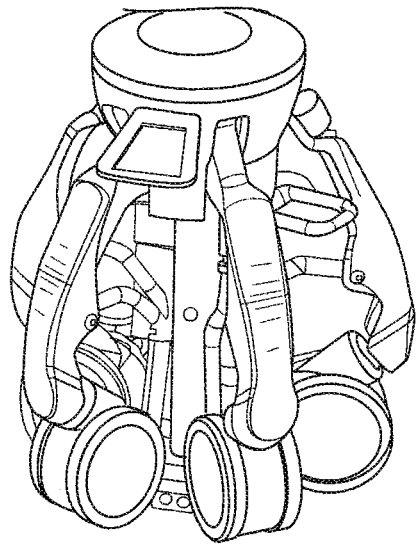
Figure 10C:
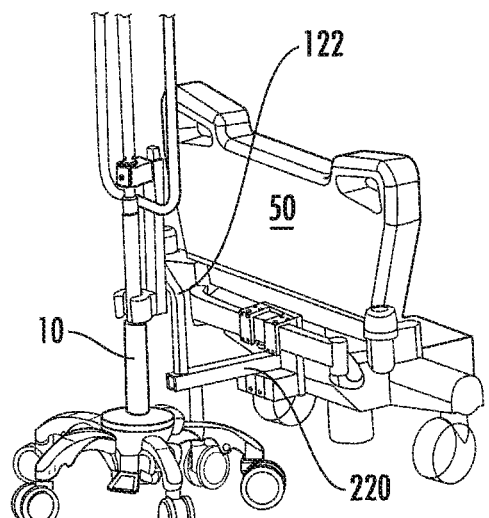
Figure 10D:
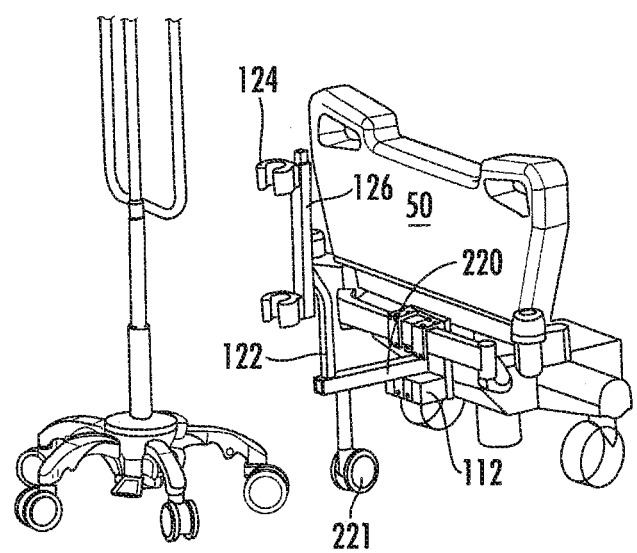

FIGS. 9A-9H illustrate a pole-bed docking configuration 300 similar to the second arm 220 discussed above with respect to the bed adapter assembly 200 for the tank 20. The pole 10 can include a circumferentially extending key 10*k* that aligns with a holding bracket 124. FIGS. 9A-9H illustrate serial operations/actions that can dock the pole to the bed, i.e., moving pole 10 into loading position adjacent the bed, aligning the pole, then pushing the pole 10 into the bed mount "clicking" attachment (FIGS. 9A-9C). Then, as shown in FIG. 9D, lift the leg release 18 safety cover, typically with the top of the foot, then pushing down on the leg release pedal under the safety cover (FIG. 9E). This action can only occur after the pole has been clicked/locked into position and preferably with at least one hand holding the pole for stability. As the legs release, the pole 10 will automatically lock into the bed mount (FIG. 9F) and the legs can then be fully retracted and locked (FIG. 9G) and a user can move the stand side to side via a swing arm 220 behind the bed while off the floor (FIG. 9G). The pivot joint/arm 129/220 can include a physical release 129r accessible by a user (FIG. 9H). For easier transport, the bed mount/docking system 300 can be posited to either side of the bed, allowing the lock associated with the release button to prevent the bed mount from rotating during transport of the bed. In this embodiment, the additional swing arm 120 is not required. FIGS. 10A-10D illustrate exemplary unloading operations that can be used to disconnect the pole from the pole-bed docking system 300. Typically, the swing arm 220 is placed in a release position at the fully extended (straight out) position (FIG. 10A), and force is applied to the down pedal (FIG. 10B) toward the ground until the legs automatically lock out and stay in the extended position, then the pole can be removed from the bed mount (FIG. 10C). The pole is then free and the bed docking system can be rotated to the side/transport position until further docking of the pole or another pole is desired.

FIGS. 11 and 12 illustrate an exemplary pole 10 with a knob 10i for adjusting a vertical height of a fluid bag halo 10s.

The above disclosure is intended to be illustrative and not exhaustive. This description will suggest many variations and alternatives to one of ordinary skill in this art. Thus, the foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the invention.

Further, the particular features presented in the dependent claims can be combined with each other in other manners within the scope of the invention such that the invention should be recognized as also specifically directed to other embodiments having any other possible combination of the features of the dependent claims. For instance, for purposes of claim support, any dependent claim which follows from an independent claim should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims).

What is claimed is:

1. A docking system for a mobile patient support apparatus comprising:
   a bracket adapted to be coupled to a side or end of the mobile patient support apparatus at a location above a floor;
   a first arm pivotably coupled to the bracket and extending outward from the mobile patient support apparatus, wherein the first arm is configured to pivot at least thirty degrees relative to the mobile patient support apparatus about a substantially vertical pivot axis;
   a second arm pivotably coupled to the bracket and extending outward from the mobile patient support apparatus, the second arm having a longer length than the first arm; and
   an upright member attached to the second arm, the upright member comprising a pole bracket for releasably engaging a pole of a medical accessory device.

2. The docking system of claim 1 wherein the first and second arms are adapted to pivot independently of each other.

3. The docking system of claim 1 wherein the second arm is configured to pivot about the substantially vertical pivot axis.

4. The docking system of claim 2 wherein the first arm is configured to pivot in a range of 90 to 180 degrees.

5. The docking system of claim 1 wherein the medical accessory device is one of an IV stand, a tray table, and a monitor support.

6. A docking system for a mobile patient support apparatus comprising:
   a bracket adapted to be coupled to a side or end of the mobile patient support apparatus at a location above a floor;
   a first arm pivotably coupled to the bracket and extending outward from the mobile patient support apparatus, wherein the first arm is configured to pivot at least thirty degrees relative to the mobile patient support apparatus about a substantially vertical pivot axis;
   a second arm pivotably coupled to the bracket and extending outward from the mobile patient support apparatus; and
   an upright member attached to the second arm, the upright member comprising a pole bracket for releasably engaging a pole of a medical accessory device; wherein the first and second arms are parallel and horizontally oriented, and wherein the first and second arms are vertically spaced apart a distance of 0.25 to 0.5 inches.

7. The docking system of claim 6 wherein the second arm is configured to pivot about the substantially vertical pivot axis, and the first and second arms are configured to lock together, to pivot in concert, and to pivot independently.

8. The docking system of claim 7 wherein the medical accessory device is one of an IV stand, a tray table, and a monitor support.

9. A docking system for a mobile patient support apparatus comprising:
   a bracket adapted to be coupled to a side or end of the mobile patient support apparatus at a location above a floor;
   a first arm pivotably coupled to the bracket and extending outward from the mobile patient support apparatus, wherein the first arm is configured to pivot at least thirty degrees relative to the mobile patient support apparatus about a substantially vertical pivot axis, the first arm including a canister bracket attached thereto, the canister bracket adapted to releasably support an oxygen canister;
   a second arm pivotably coupled to the bracket and extending outward from the mobile patient support apparatus; and an upright member attached to the second arm, the upright member comprising a pole bracket for releasably engaging a pole of a medical accessory device.

10. The docking system of claim 9 wherein the second arm has a length sufficient to allow the upright member to be positioned adjacent to, and behind, an oxygen canister supported in the canister bracket.

11. The docking system of claim 10 wherein the second arm is configured to pivot about the substantially vertical pivot axis, and the first and second arms are configured to lock together, to pivot in concert, and to pivot independently.

12. The docking system of claim 11 wherein the medical accessory device is one of an IV stand, a tray table, and a monitor support.

13. A docking system for a mobile patient support apparatus comprising:
- a bracket adapted to be coupled to a side or end of the mobile patient support apparatus at a location above a floor;
- a first arm pivotably coupled to the bracket and extending outward from the mobile patient support apparatus, wherein the first arm is configured to pivot at least thirty degrees relative to the mobile patient support apparatus about a substantially vertical pivot axis;
- a second arm pivotably coupled to the bracket and extending outward from the mobile patient support apparatus; and
- an upright member attached to the second arm, the upright member comprising a pole bracket for releasably engaging a pole of a medical accessory device, the upright member having a curvilinear shape configured to position the pole bracket outward from the mobile patient support apparatus a greater distance than a free end of the second arm.

14. The docking system of claim 13 wherein the second arm is configured to pivot about the substantially vertical pivot axis, and the first and second arms are configured to lock together, to pivot in concert, and to pivot independently.

15. The docking system of claim 14 wherein the medical accessory device is one of an IV stand, a tray table, and a monitor support.

16. A docking system for a mobile patient support apparatus comprising:
- a bracket adapted to be coupled to a side or end of the mobile patient support apparatus at a location above a floor;
- a first arm pivotably coupled to the bracket and extending outward from the mobile patient support apparatus, wherein the first arm is configured to pivot at least thirty degrees relative to the mobile patient support apparatus about a substantially vertical pivot axis;
- a second arm pivotably coupled to the bracket and extending outward from the mobile patient support apparatus; and
- an upright member attached to the second arm, the upright member comprising a pole bracket for releasably engaging a pole of a medical accessory device; wherein the first and second arms are configured to lock together, to pivot in concert, and to pivot independently.

17. The docking system of claim 16 wherein the medical accessory device is one of an IV stand, a tray table, and a monitor support.

18. A docking system for a mobile patient support apparatus comprising:
- a bracket adapted to be coupled to a side or end of the mobile patient support apparatus at a location above a floor;
- a first arm pivotably coupled to the bracket and extending outward from the mobile patient support apparatus, wherein the first arm is configured to pivot at least thirty degrees relative to the mobile patient support apparatus about a substantially vertical pivot axis;
- a second arm pivotably coupled to the bracket and extending outward from the mobile patient support apparatus; and
- an upright member attached to the second arm, the upright member comprising a pole bracket for releasably engaging a pole of a medical accessory device, wherein the upright member has a curvilinear shape with a first vertical length that merges into a second angled length that merges into a third vertical length, and wherein the pole bracket is on the third vertical length.

19. The docking system of claim 18 wherein the second arm is configured to pivot about the substantially vertical pivot axis, and the first and second arms are configured to lock together, to pivot in concert, and to pivot independently.

20. The docking system of claim 19 wherein the medical accessory device is one of an IV stand, a tray table, and a monitor support.

* * * * *